United States Patent
Galbierz et al.

(10) Patent No.: US 10,653,404 B2
(45) Date of Patent: May 19, 2020

(54) BIDIRECTIONAL CROSS-MIDLINE RETRACTOR/STABILIZER FOR EXCESSIVE AND/OR REDUNDANT TISSUE

(71) Applicant: GSQUARED MEDICAL LLC, Brentwood, TN (US)

(72) Inventors: Thomas R. Galbierz, Brentwood, TN (US); Michael A. Galbierz, St. Louis, MO (US)

(73) Assignee: GSQUARED MEDICAL LLC, Brentwood, TN (US)

( * ) Notice: Subject to any disclaimer, the term of this patent is extended or adjusted under 35 U.S.C. 154(b) by 77 days.

(21) Appl. No.: 15/571,778

(22) PCT Filed: Apr. 28, 2016

(86) PCT No.: PCT/US2016/029833
§ 371 (c)(1),
(2) Date: Nov. 3, 2017

(87) PCT Pub. No.: WO2016/182752
PCT Pub. Date: Nov. 17, 2016

(65) Prior Publication Data
US 2019/0125326 A1    May 2, 2019

Related U.S. Application Data

(60) Provisional application No. 62/161,055, filed on May 13, 2015, provisional application No. 62/259,216, filed on Nov. 24, 2015.

(51) Int. Cl.
*A61B 17/02* (2006.01)
*A61B 46/20* (2016.01)
(Continued)

(52) U.S. Cl.
CPC .............. *A61B 17/02* (2013.01); *A61B 46/20* (2016.02); *A61B 2017/00022* (2013.01);
(Continued)

(58) Field of Classification Search
CPC ..... A61B 17/02; A61B 17/0218; A61B 46/20; A61F 5/37
(Continued)

(56) References Cited

U.S. PATENT DOCUMENTS 6,572,541 B1    6/2003   Petersvik
6,814,700 B1 *  11/2004  Mueller ............. A61B 17/0293
                                                      600/201
(Continued)

FOREIGN PATENT DOCUMENTS

WO    2014120746 A1    8/2014

OTHER PUBLICATIONS

International Search Report for corresponding PCT/US2016/029833 dated Aug. 5, 2016.
(Continued)

*Primary Examiner* — Si Ming Ku
(74) *Attorney, Agent, or Firm* — Sandberg Phoenix & von Gontard, P.C.

(57) ABSTRACT

A die-cuttable retractor/stabilizer for repositioning and stabilizing excessive and/or redundant tissue comprises a top layer and a backing layer. An adhesive on the top layer is exposed when the backing layer is separated from the top layer to enable the top layer to be applied to a surface. The retractor/stabilizer comprises a body having a top edge, side edges and a bottom edge. A tab portion is associated with the removable panel, such that the backing layer remains with the tab portion and the tab portion can be used to remove at least a portion of the backing layer from the retractor/stabilizer body. The retractor/stabilizer additionally includes
(Continued)

at least one protected grasping/holding area located at an edge or corner of said retractor/holding area as the backing layer is removed from the body to provide a protected holding area once the backing layer has been removed from the body.

28 Claims, 5 Drawing Sheets

(51) Int. Cl.
    *A61B 17/00*     (2006.01)
    *A61B 90/00*     (2016.01)

(52) U.S. Cl.
    CPC .............. *A61B 2017/00039* (2013.01); *A61B 2017/00084* (2013.01); *A61B 2017/00119* (2013.01); *A61B 2017/00221* (2013.01); *A61B 2017/00893* (2013.01); *A61B 2017/00907* (2013.01); *A61B 2017/00951* (2013.01); *A61B 2017/0212* (2013.01); *A61B 2046/205* (2016.02); *A61B 2090/0808* (2016.02)

(58) Field of Classification Search
    USPC ........................................................ 600/202
    See application file for complete search history.

(56) References Cited

U.S. PATENT DOCUMENTS

| | | |
|---|---|---|
| 2004/0186356 A1 | 9/2004 | O'Malley et al. |
| 2008/0103366 A1* | 5/2008 | Banchieri ................ A61B 1/32 600/208 |
| 2013/0327342 A1 | 12/2013 | Watschke et al. |
| 2014/0364696 A1 | 12/2014 | Blurton et al. |

OTHER PUBLICATIONS

Written Opinion for corresponding PCT/US2016/029833 dated Aug. 5, 2016.
International Preliminary Report on Patentability for corresponding PCT/US2016/029833 dated Jul. 14, 2017.

* cited by examiner

BIDIRECTIONAL CROSS-MIDLINE RETRACTOR/STABILIZER FOR EXCESSIVE AND/OR REDUNDANT TISSUE

CROSS-REFERENCE TO RELATED APPLICATIONS

This application is the US National Stage application under 35 U.S.C. § 371 of International App. No. PCT/US2016/029833 filed Apr. 28, 2016 which claims priority to U.S. App. Nos. 62/161,055 filed May 13, 2015 and 62/259,216 filed Nov. 24, 2015, both of which are entitled "Bidirectional Cross-Midline Retractor/Stabilizer For Excessive And/Or Redundant Tissue" and both of which are incorporated herein by reference.

STATEMENT REGARDING FEDERALLY SPONSORED RESEARCH OR DEVELOPMENT

Not Applicable.

BACKGROUND OF THE INVENTION

This application relates to a retractor/stabilizer that can be used to displace, retract and/or stabilize excessive and/or redundant tissue (such as adipose tissue, panniculus tissue, etc.) to facilitate access to target sites and/or to facilitate noted medical procedures.

In WO 2014/120746, entitled "Retractor/Stabilizer For Excessive And/Or Redundant Tissue And Method Of Use" (which is incorporated by reference herein), we disclose a retractor/stabilizer for excessive and/or redundant tissue. The retractor/stabilizer disclosed therein spans substantially across a patient's abdomen. That retractor/stabilizer is applied by pulling the retractor/stabilizer towards the patient's head (i.e., in a cephalad direction). The stabilizer disclosed therein works well and facilitates many medical procedures. However, it is not always necessary to retract/stabilize a patient's full panniculus. This would be the case, for example, during hip surgery, or other surgical or medical procedures in which access to only one side of the patient is required.

SUMMARY

Briefly stated, a retractor/stabilizer for repositioning and stabilizing excessive and/or redundant tissue is provided. The retractor/stabilizer comprises a top layer and a backing layer. The top layer has an adhesive applied thereto which is exposed when the backing layer is separated from the top layer to enable the top layer to be applied to a surface; the retractor/stabilizer comprises:
  a body having a top edge, side edges and a bottom edge;
  an lower grasping panel extending from a lower edge of the body proximate an outer end of the lower edge;
  at least one upper protected grasping/holding area located proximate an inner end or corner of the top edge the retractor/stabilizer proximate and offset from an outer edge of the lower grasping panel, such that when the retractor/stabilizer is stretched by pulling on the at least one protected grasping/holding area, the retractor will be stretched in a direction offset from a vertical axis of the retractor/stabilizer;
  the at least one upper protected grasping/holding area and the lower grasping panel are each defined in part by a back cut separating the backing layer of the lower grasping panel and the backing layer of the at least one grasping area from the backing layer of the body; whereby the backing layer of the lower grasping panel and the backing layer of the at least one grasping area remains with the at least one protected grasping/holding area and the lower grasping panel when the backing layer is removed from the body of the retractor/stabilizer.

The retractor/stabilizer can be provided with a tab portion that is associated with the removable panel. The backing layer of the tab portion is integral with the backing layer of body portion and the retractor/stabilizer includes a cut in the top layer which separates the top layer of the tab portion from the top layer of the body portion.

In one variation, the lower grasping panel can extend from an outer end of the lower edge; and in another variation, the lower grasping panel can comprise a bottom portion of the body (such that the edge of the lower grasping panel defines an edge of the retractor/stabilizer).

In accordance with an aspect of the retractor stabilizer, the retractor/stabilizer comprises a top layer and a backing layer wherein the top layer has an adhesive applied thereto which is exposed when the backing layer is separated from the top layer to enable the top layer to be applied to a surface. The retractor/stabilizer comprises:
  a body having a top edge, an inner side edge, an outer side edge, and a bottom edge; and
  at least one lower grasping panel extending from a lower edge of the body at an outer end of the lower edge; the at least one lower grasping panel being defined in part by a back cut separating the backing layer of the lower grasping panel from the backing layer of the body; whereby the backing layer of the lower grasping panel remains with the lower grasping panel when the backing layer is removed from the body of the retractor/stabilizer.

In accordance with an aspect of the retractor/stabilizer, the retractor/stabilizer comprises a top layer and a backing layer wherein the top layer has an adhesive applied thereto which is exposed when the backing layer is separated from the top layer to enable the top layer to be applied to a surface. The retractor/stabilizer comprises:
  a body having a top edge, side edges and a bottom edge; the body defining a bottom grasping area portion, a positioning portion above the grasping area portion, and a main portion above the positioning portion; the backing layer of the three portions being separated by back cuts; the main portion defining two spaced apart anchor points; and
  a tab portion associated with each portion of the body; the backing layer of the tab portion being integral with the backing layer of body portion and the retractor/stabilizer including a cut in the top layer which separates the top layer of the tab portion from the top layer of the body portion, such that pulling the tab will separate the backing layer from the top layer.

The retractor/stabilizer can include at least one protected grasping/holding area located at an edge or corner of the main portion. The at least one protected grasping/holding area is defined in part by a back cut separating the backing layer of the lower grasping panel and the backing layer of the at least one grasping area from the backing layer of the body; whereby the backing layer of the at least one grasping area remains with the at least one protected grasping/holding area when the backing layer is removed from the body of the retractor/stabilizer.

The body main portion can include a first part extending upwardly from the positioning portion and a second part extending to the left or right of the first part, such that an end of the second part is spaced horizontally from an edge of the first part.

In one embodiment, the body can be generally Y-shaped and define a first anchor lobe and a second anchor lobe. In this embodiment, the at least one grasping area comprises a grasping area at an end of each of the lobes. In one variation, the inner side edge of the body is generally straight. In another variation, the retractor is generally symmetrical about an axis of the retractor body, and the side edges of the retractor generally define a concave curve.

In one variation, the bottom portion of the body can define two spaced apart grasping areas.

In a variation of the retractor/stabilizer, a bottom edge of the positioning portion is defined by cut-lines extending generally diagonally downwardly from opposite side edges of the retractor/stabilizer body toward an approximate center of the bottom edge.

Any of the above-noted retractor/stabilizers can include at least one anchor point at an upper end of the retractor/stabilizer on a side of the retractor/stabilizer opposite the at least one lower grasping panel. As can be appreciated, this grasping area is remote from the anchor area. The retractor/stabilizer can also include a grasping area that is proximate the at least one anchor point.

In an embodiment of the retractor/stabilizer, the lower grasping panel defines a lower anchor point, and the upper and lower anchor points are on opposite sides of the retractor/stabilizer.

According to an aspect of any of the above-noted retractor/stabilizers, the retractor/stabilizers can include a lower grasping tab portion associated with the lower grasping panel; the backing layer of the lower grasping panel portion being integral with the backing layer of lower grasping panel and the retractor/stabilizer including a cut in the top layer which separates the top layer of the lower grasping tab portion from the top layer of the lower grasping panel.

In accordance with an aspect of any of the above retractor/stabilizers, the tab portion can define either an outboard tab which extends from the body portion or an inboard tab in which an outer edge of the tab portion is generally flush with an outer edge of the body portion.

In accordance with an aspect of any of the above retractor/stabilizers, the retractor/stabilizer can further comprise at least one protected grasping/holding area located at an edge or corner of the retractor/stabilizer. The grasping area is configured to be graspable by a technician without the technician contacting exposed adhesive of the top layer.

In accordance with an aspect of any of the above retractor/stabilizers, the bottom edge of the body of the above retractor/stabilizers can define a straight line or a downwardly directed curve or arc. In one variation, the bottom edge can slope from one side edge of the body to an opposite side edge of the body.

In accordance with an aspect of any of the above retractor/stabilizers, the top layer of the retractor/stabilizers can be made from a flexible or semi-rigid material comprised of one or more of the following: a plastic, a natural cloth/fabric, a man-made cloth/fabric, spandex, a silicone matting, paper, plastic, foam, and film.

In accordance with an aspect of any of the above retractor/stabilizers, the top layer of the retractor/stabilizers can be vapor-permeable and breathable or can be vapor-impermeable.

In accordance with an aspect of any of the above the retractor/stabilizers, the top layer of the retractor/stabilizers can have a machine direction that runs generally diagonally of a vertical of axis the retractor/stabilizer.

In accordance with an aspect of the retractor/stabilizer, the at least one protected grasping/holding area can be positioned, such that when the retractor/stabilizer is applied to a patient, and when the at least one protected grasping/holding area is pulled, the retractor/stabilizer will stretch in a direction generally diagonal relative to the vertical axis of the retractor/stabilizer and either generally parallel to, or generally orthogonal to, the machine direction.

In accordance with an aspect of any of the above retractor/stabilizers, the top layer of the retractor/stabilizers can have a machine direction that runs generally vertically of the retractor/stabilizer body.

In accordance with an aspect of any of the above retractor/stabilizers, the top layer and/or the adhesive of the retractor/stabilizers can contain a pharmaceutical agent that is delivered to the patient's skin when the retractor/stabilizer is applied to a patient.

In accordance with an aspect of any of the above retractor/stabilizers, the grasping area of the retractor/stabilizers can be integral with the body, in which case, the grasping area is defined in part by a cut in the backing layer which divides the backing layer of the grasping area from the rest of the backing layer.

In accordance with an aspect of any of the above retractor/stabilizers, the grasping area of the retractor/stabilizers is defined (1) by a portion of the top layer being folded or hemmed such that the top layer adhesive is turned back on itself, face to face, to produce the adhesive-free grasping area or (2) by a separate piece which is adhered to the retractor/stabilizer body.

In accordance with an aspect of the retractor/stabilizer, the retractor stabilizer includes at least one tab associated with the backing layer and positioned at an edge of the body; whereby pulling on the tab in a direction away from the top layer will remove the backing layer from the top layer. The at least one tab is either an inboard tab having an outer edge that is generally flush with the edge of the body at which the tab is located or an outboard tab which extends from an edge of the body.

In accordance with an aspect of any of the retractor/stabilizers, the tab is integral with the body and is defined in part by a cut in the top layer such that the backing layer portion of the tab remains connected to the backing layer of the panel with which the tab is associated, yet the top layer of the tab is separated from the top layer of the body with which the tab is associated.

In accordance with an aspect of any of the retractor/stabilizers, the retractor/stabilizer further comprises a back cut in the backing layer extending from one side to the other, to separate the backing layer into an upper panel and a lower panel. The at least one tab comprises at least one upper panel tab associated with the backing layer upper panel and at least one lower panel tab associated with the backing layer lower panel. The side-to-side back cut can define a curvature that simulates the curvature of a patient's abdomen and/or other anatomy of the patient.

The retractor/stabilizer can further comprise:
  a lower panel back cut in the backing layer lower panel extending from the bottom edge to a point proximate the side-to-side back cut; the first lower panel back cut dividing the lower panel in to at least a lower panel positioning portion and a lower panel second portion;
  a positioning portion tab associated with the lower panel positioning portion, the body including a cut in the top layer such that pulling on the positioning portion tab in a direction away from the top layer will remove the backing layer lower panel positioning portion from the top layer; and a lower panel second portion tab associated with the lower panel second portion; the body including a cut in the top layer such that pulling on the lower panel second portion tab in a direction away from the top layer will remove the backing layer lower panel second portion from the top layer.

In the retractor/stabilizer, the at least one upper panel tab can be located at one or both of the side edges and the upper edge of the body.

In accordance with an aspect of any of the above retractor/stabilizers, the retractor/stabilizer can include an indicator/sensor adapted to monitor a parameter chosen from the group consisting of elongation and/or stretch of the retractor/stabilizer, ambient and physiological aspects of the patient's wound; the indicator/sensor being adapted to indicate if the monitored parameter exceeds or falls below a predetermined threshold. The ambient and physiological aspects that are monitored can include, for example, the presence of biological (i.e., bacterial or viral) agents, physiological data (i.e., blood pressure, skin temperature at the incision site, heart rate), or concentrations of specific chemicals, vapors or gases (such as $H_2O$, $O_2$ or $CO_2$). An indicator/sensor that monitors elongation/stretch of the retractor/stabilizer can be a mechanical indicator incorporated into the retractor/stabilizer. Any of the sensors can be electrical sensors which transmit to a receiver a signal indicative of the parameter being monitored. The receiver can issue a visual, tactile (vibratory) or audible alert if the monitored parameter exceeds or falls below the predetermined threshold. Further, the receiver can include a transmitter to transmit data of the monitored parameter to a healthcare provider.

Methods of use of the retractor/stabilizers are also disclosed. In accordance with one aspect, the method comprises adhering a tension member to the patient such that the tension member extends diagonally across a patient midline, wherein the tension member comprises a sheet of material having a surface coated with an adhesive which will adhere to the dermis of a patient. The step of adhering the tension member to the patient includes:

adhering a first portion of the tension member to redundant and/or excessive tissue of the patient such that a lower outer edge of the tension member is proximate an inguinal crease of the patient;

pulling an upper inner edge of the tension member bidirectionally in a both cephalad and diagonal direction; and adhering a second portion of the tension member to an anchor point on the patient; the anchor point being across the patient's midline proximate the xiphoid process/thoracic cavity near the shoulder;

whereby the excessive or redundant tissue pulls against the second portion of the tension member thereby placing the tension member in tension.

According to an aspect of the method, the tension member is self-contained, and is secured only to the patient.

According to an aspect of the method the excessive and/or redundant tissue is a panniculus, and the step of adhering the first portion of the tension member to the excessive and/or redundant tissue encasing the radius of the panniculus.

According to an aspect of the method, the tension member conforms to the shape of the patient upon application of the tension member to the patient and supports the excessive and/or redundant tissue after application.

According to an aspect of the method, the anchor point is about 5° to about 45° across the patient's midline.

According to an aspect of the method, the anchor point is about 10° to about 20° across the patient's midline.

According to an aspect of the method, the retractor/stabilizer is applied to the patient at an angle of about 5° to about 40° relative the patient's midline.

In accordance with another aspect, there is disclosed a method of reducing the distance to a target site in a patient having excessive and/or redundant tissue. This method comprises adhering a one-piece tension member to the patient, wherein the tension member comprises a sheet of material having a surface substantially fully coated with an adhesive which will adhere to the dermis of a patient. The step of adhering the tension member to the patient includes:

adhering a first portion of the tension member to redundant and/or excessive tissue of the patient; and adhering a second portion of the tension member to an anchor point on the patient; the anchor point being spaced from the redundant and/or excessive tissue;

whereby the tension member is adhered to the patient substantially over the entire surface area of the tension member, and whereby the excessive or redundant tissue pulls against the second portion of the tension member thereby placing the tension member in tension thereby minimizing and reducing the distance between the dermis and the target area.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figure 1:
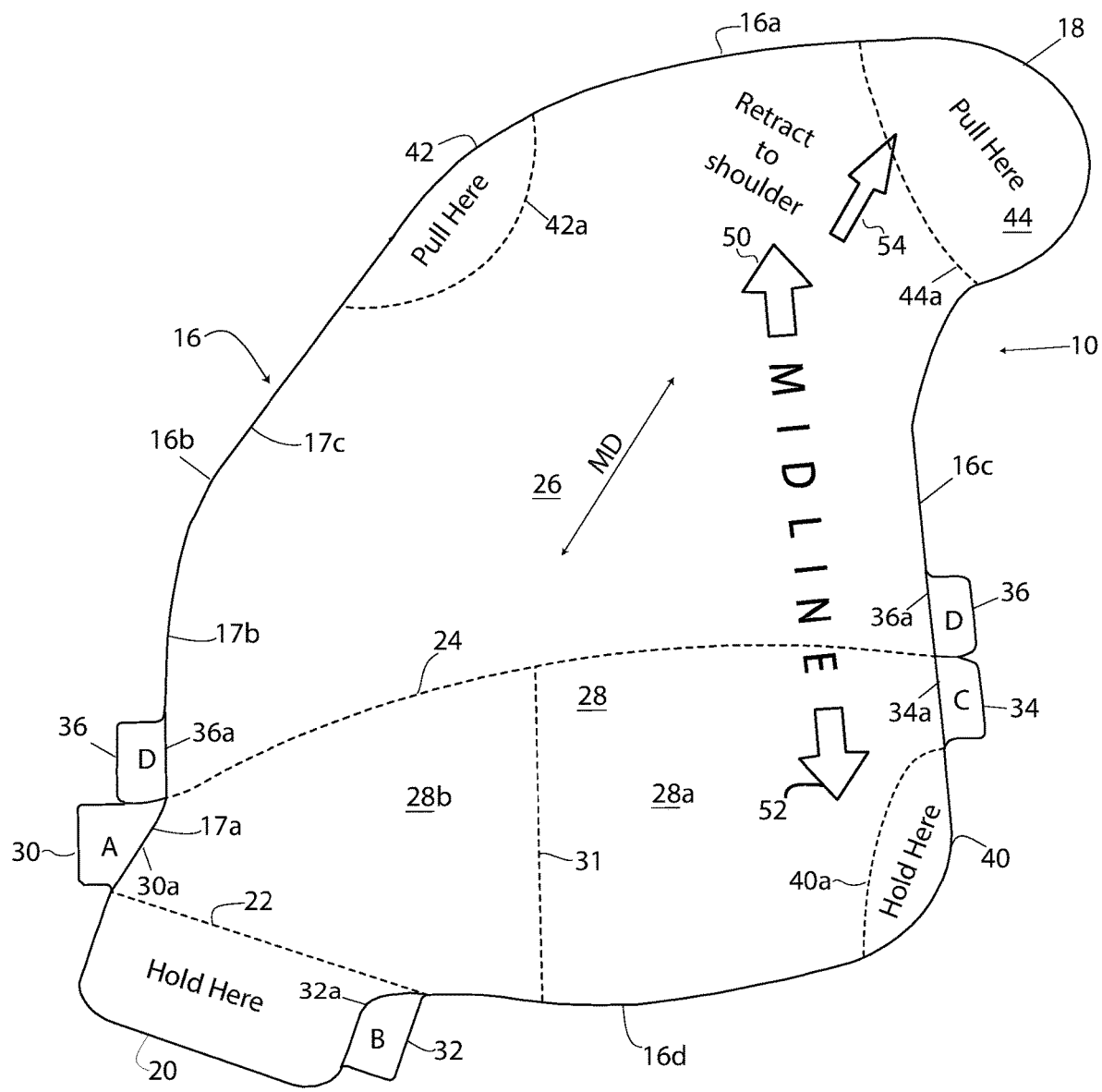
FIG. 1 is a plan view of a first embodiment of a retractor/stabilizer for excessive and/or redundant tissue.

The following detailed description illustrates the retractor/stabilizer by way of example and not by way of limitation. This description will clearly enable one skilled in the art to make and use the claimed retractor/stabilizer, and describes several embodiments, adaptations, variations, alternatives and uses of the claimed retractor/stabilizer, including what we presently believe is the best mode of carrying out the claimed invention. Additionally, it is to be understood that the claimed retractor/stabilizer is not limited in its application to the details of construction and the arrangements of components set forth in the following description or illustrated in the drawings. The claimed retractor/stabilizer is capable of other embodiments and of being practiced or being carried out in various ways. Also, it is to be understood that the phraseology and terminology used herein is for the purpose of description and should not be regarded as limiting.

Figure 2:
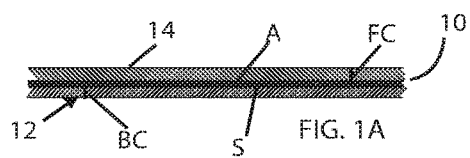
FIG. 2 is a cross-sectional schematic view of the retractor/stabilizer to show the two layers of the retractor/stabilizer, as provided.

A retractor/stabilizer 10 is shown in plan view in FIG. 1, and in an enlarged illustrative cross-section in FIG. 2. The retractor/stabilizer is formed (such as by die cutting) of a multi-ply sheet assembly comprised of a backing layer, release layer or liner 12 to which a top layer 14 is adhered by means of an adhesive A on a bottom surface of the top layer. The adhesive preferably is applied to substantially the entire bottom surface of the top layer. The adhesive is typically a pressure-sensitive adhesive (PSA), but can be an acrylate adhesive, a silicone adhesive or a co-adhesive. The top layer can have several properties/characteristics:

- The top layer can be made from a film, cloth/fabric (formed from either natural or man-made materials), spandex, a silicone matting, paper, plastic, foam, plastic, compounds/composites, or any other desired material which will work suitably as described below.
- The top layer can be single ply or multi-ply.
- The top layer can be a woven or nonwoven mesh or it can be solid or continuous.
- The top layer can be breathable (vapor permeable) or vapor impermeable.
- The top layer can be made from a material which can be incised (e.g., cut or sliced), punctured, perforated or penetrated with an instrument or retractor/stabilizer after the top layer has been applied to the patient. Although not typical, incising of the top layer after application to the patient may be necessary depending on the proximity of the retractor/stabilizer to the incision area.
- The top layer can be transparent, translucent or opaque.
- The top layer can be provided with reinforcing sections or strips made of either the same material as the top layer or from a different material. These reinforcing sections or strips can be applied to the top layer of the retractor/stabilizer. Alternatively, the top layer of the retractor/stabilizer can have reinforcing threads or fibers incorporated into it. These reinforcing threads or fibers can be parallel to the machine direction of the top layer, perpendicular to the machine direction of the top layer, or at an angle (other than about 0° or about 90°) to the machine direction of the top layer. As another alternative, such reinforcing threads or fibers need not be parallel to each other, and can crisscross each other or can form random configurations (be spaghetti-like) in the top layer.
- A portion (or all of) the top layer and/or adhesive layer can be impregnated or infused with a pharmaceutical agent for delivery of the agent to the patient, such that the retractor/stabilizer functions as a transdermal delivery retractor/stabilizer for treatment of a wound, patient or both.
- The retractor/stabilizer top layer can include an indicator to show evidence of an elongation, stretch, biological (i.e., bacterial or viral) agent, temperature, chemical, vapor or gas (such as $H_2O$, $O_2$ or $CO_2$) concentrations, rates or values. Alternatively, the top layer can be provided with a sensor, as discussed more fully below, which can transmit data indicative of any of the foregoing.

Various combinations of top layer and adhesive would allow for the retractor/stabilizer to be autoclaved and reused. However, the retractor/stabilizer is intended to be a single-use retractor/stabilizer. Preferably, the film/top layer is latex free. An anti-static coating can be applied to the top layer if desired. An anti-static agent can also be included with the adhesive. Further, the top layer can be provided with anti-microbial and/or antibacterial agents, which can, for example, be mixed in with, or applied to the surface of, the adhesive, such that the antimicrobial and/or antibacterial agents are in contact with the patient's skin during use. The retractor/stabilizer is preferably sterilized, such as by gamma radiation, and is sterilizable.

In one illustrative embodiment, the retractor/stabilizer can be made from a product such as 3M 9865 medical grade tape (available from 3M) or MACTac TM1030 (available from MACtac North America, of Stow, Ohio, US). In the 3M medical tape (the 3M 9865 medical grade tape), the release layer 12 (or backing layer) is currently comprised of 63 lb. poly-coated Kraft paper with a thin (4.9 mils/0.12 mm) silicone coating S on one side of the backing paper and a 3.0 mil (0.08 mm) translucent polyethylene film top layer 14 with an adhesive coating A applied to one side of the top layer. The adhesive coating A substantially covers the entire surface of the film to which it is applied. Similarly, the silicone coating covers substantially the entire surface of the backing layer to which it is applied. The adhesive is an acrylate adhesive which is designed for medical/surgical use. As can be appreciated, the top layer is applied to the Kraft paper liner with the adhesive side of the top layer in contact with the silicone coated side of the paper liner. When the liner is removed from the top layer, the adhesive side of the top layer will be exposed for application of the top layer to a desired surface (such as a patient's body).

To enable use of the retractor/stabilizer, a series of cuts are formed in the blank from which the retractor/stabilizer is formed to facilitate removal of the backing layer from the top layer in such a way so as to avoid, as much as possible, the medical practitioner's gloves from contacting the adhesive during application of the retractor/stabilizer to a patient. FIG. 2 shows that some cuts are top or face cuts FC which extend just through the top layer 14 (but not through the backing layer 12), and that other cuts are back cuts BC which extend just through the backing layer 12, but not through the top layer 14. Back cuts are used to form integral protected grasping areas of the retractor/stabilizer. The back cuts BC which form or define the grasping areas allow for the backing layer 12 to remain with the top layer 14 in these areas when the backing layer proximate the grasping area is removed. This allows for medical personnel to hold and position the retractor/stabilizer when a portion, or all, of the backing layer 12 (except for the backing layer in the protected grasping areas) has been removed from the top layer without having their gloves contact the adhesive. Back cuts can also be formed to divide the backing layer into discrete sections or panels which can be removed independently of each other.

To facilitate removal of the backing layer, each backing layer panel can be provided with at least one tab. The tab enables the technician to remove the backing layer from the top layer of the retractor/stabilizer without coming into contact with the adhesive of the top layer. In a preferred embodiment, the tabs are formed from the sheet from which the retractor/stabilizer is formed. That is, the tabs are integral with the body of the retractor/stabilizer. To this end, the tabs can be defined by face slices or cuts FC at an end of each tab where the tab joins the body of the retractor/stabilizer. These face cuts cause the top layer 14 to remain with the backing layer 12 in the area of the tab. Thus, the medical personnel can simply grasp a tab and pull downwardly to separate the backing layer 12 (or a portion of the backing layer) from the top layer 14. These tabs allow for the practitioner to remove the backing layer without his or her gloves contacting the adhesive of the top layer. In another embodiment of the tabs, the tabs can be formed separately from the retractor/stabilizer body (i.e., the tabs are not integral with the retractor/stabilizer) and are adhered to the backing layer of the retractor/stabilizer. If desired, the converting die which forms the retractor can be constructed to remove the top layer 14 from the release layer 12 in the tabs when the retractor is formed. This would eliminate the possibility of the top layer of the tab inadvertently separating from the bottom layer of the tab during a procedure. However, in view of the fact that an adhesive (albeit a weak adhesive) is holding the top layer to the release layer, inadvertent separation of the tab top layer from the tab bottom layer is believed to be unlikely.

Unless otherwise noted, the various slices or cuts are all through cuts. That is, the back cuts extend through the backing layer (but not through the top layer) and the face cuts extend through the top layer (but not through the backing layer). Full cuts, which extend through both the top layer and the backing layer are noted in certain circumstances. Thus, there is no weeding, folding, bending or crack back needed to operate the tabs and/or remove the backing layer. In FIG. 1, the internal lines which are dashed (i.e., - - -) are back cuts and the internal lines which are solid (i.e., —) are face cuts (unless noted to be full cuts).

The retractor/stabilizer is initially described for use in retracting and stabilizing the pannus or panniculus of a patient. However, the retractor/stabilizers disclosed and described below can be used with virtually any procedure in which excessive and/or redundant tissue must be moved to enable access to the procedural/target site. Such procedures include, in addition to retraction of the pannus, mapping, electrode placement, monitoring, fetal ultrasound or sonography, laparotomies (C-sections, total abdominal hysterectomies (TAH), hernias, bowel resections, etc.), incision/wound care, vascular access (e.g., to the femoral artery in the area of the groin for interventional cardiology, infusion, injection, or infiltration for example), access for nerve block and similar techniques used during anesthesiology and/or for pain management, radiology/interventional radiology, orthopedic and neurological procedures (e.g., spinal taps), plastic surgery (e.g., breast tissue management), ENT procedures and trauma procedures.

Turning to FIG. 1, a retractor/stabilizer 10 has a body 16 defining an upper edge 16a, an inner side edge 16c, an outer side edge 16b and a lower edge 16d. As will become apparent below, the retractor stabilizer 10 can be sized and shaped to cover a right portion or a left portion of a patient's pannus. Thus, as used in this application, "outer" means towards the right or left side of the patient and "inner" means toward the mid-line of the patient when the retractor/stabilizer is applied to the patient. The retractor/stabilizer shown in FIG. 1 is a patient's "right-side" retractor/stabilizer. A patient's "left-side" retractor/stabilizer is not shown, but is a mirror image of the "right-side" retractor/stabilizer. With respect to FIG. 1, the "outer" side edge 16b is the left side edge of the figure and the "inner" side edge 16c is the right side edge of the figure. It will be appreciated, that in the mirror image right side retractor, the inner and outer side edges will be opposite. That is, the "outer" side edge will be the right side edge and the "inner" side edge will be the left side edge.

As seen, the outer side edge 16b includes a lower inwardly sloping portion 17a at the bottom of the body 16, a middle generally vertical portion 17b extending upwardly from the lower portion 17a, and an upper inwardly sloping portion 17c extending from the middle portion 17b. The outer side edge upper portion 17c intersects with the upper edge 16a. The upper edge 16a and the outer side edge portions 17c and 17b in combination give the appearance of a generally curved edge. The lower edge 16d of the body is shown to define a convex (or downwardly extending) arc section. However, it will be appreciated that the lower edge could be generally straight or even concavely (upwardly) curved if desired. The corners of the retractor/stabilizer 10 are shown to be radiused or curved. This avoids the tendency for the top layer to lift off the patient's skin due to the concentration of stresses and forces as could happen if the corners were sharper or generally right-angled corners. However, the corners could be sharp, if desired. A shoulder 18 or finger extends generally perpendicularly to the inner side edge 16c at the upper end of the inner side edge. As seen, the edge of the shoulder 18 is a continuation of the upper edge 16a. The edge of the shoulder 18 is generally semi-circular, and curves around to join with the inner side edge 16c. The retractor/stabilizer 10 is sized, from side-to-side to extend generally from the patient's side to slightly beyond the patient's midline. Thus, the right side retractor will extend generally from the patient's right side to across the patient's midline. Similarly, the left side retractor will extend generally from the patient's left side to across the patient's midline. As can be appreciated, it is not intended that the right and left side retractors be used together. Although, in proper situations, this would be possible.

In addition, an inguinal panel/lower grasping area 20 extends downwardly from the body at the lower end of the outer side edge 16b and the outer end of the lower edge 16d. The backing of the inguinal panel 20 is separated from the backing of the body by a back cut 22. The back cut 22 is shown to define a generally straight line which forms an almost right angle with the lower portion 17a of the outer side edge 16b and defines an obtuse angle with the bottom edge 16d of the retractor body 16. The angle defined by the junction of the body bottom edge 16d and the cut line 22 is sufficiently large that the cut line 22 is nearly a continuation of the curvature of the bottom edge 16d. The inguinal panel is shown to be generally rectangular. However, the panel can have other shapes. For example, the bottom edge of the inguinal panel 20 can be curved or sloped, such that the inguinal panel will approximately match the contours and creases of the patient's body at the inguinal crease.

A back cut 24 extends across the width of the body from the outer side edge 16b to the inner side edge 16c to divide the backing layer 12 into an upper panel 26 and a lower panel 28. This back cut 24 is shown to be slightly upwardly curved. The back cut 24 defines a concave radius or curvature that simulates or represents the curvature of a patient's abdomen to facilitate the removal of the backing layer upper panel 26 during application of the retractor/stabilizer to a patient. As shown, the backing layer lower panel 28 comprises about the lower one-third of the body 16. A back cut 31 extends upwardly from approximately the center of the bottom edge 16d to the back cut 24. The back cut 31 divides the backing lower panel 28 into an inner portion 28a and an outer portion 28b.

As can be appreciated, to apply the adhesive top layer 14 to a patient, the backing layer 12 must be removed. The retractor/stabilizer is provided with a series of tabs which enable the practitioner to remove the various backing panels from the top layer while avoiding contact of the practitioner's gloves with the adhesive of the top layer. Each backing layer panel has at least one tab associated therewith. Thus, the retractor/stabilizer includes an A-tab 30 associated with the outer lower panel 28*b* and positioned at the bottom of the outer side edge 16*b* between the top of the inguinal panel 20 and the cut line 24; a B-tab 32 associated with the inguinal panel 20 and positioned at an inner side edge of the inguinal panel 20; a C-tab 34 associated with the inner bottom panel 28*a* and positioned along the inner side edge 16*c* just below the cut line 24; and D-tabs 36 associated with the upper panel 26 and positioned on the inner and outer side edges 16*c*, 16*b* just above the cut line 24. As can be seen, the D-tabs 36 are essentially just above the A-tab and the C-tab. The D-tabs could be spaced from the respective A-tab and C-tab. However, this positioning eases cutting of the retractor/stabilizer 10 from a blank. The D-tabs are separated from their respective A-tab and C-tab by full cuts which extend through both layers of the retractor/stabilizer. The upper layers of the tabs are separated from the upper layer of the body by face cuts 30*a*, 32*a*, 34*a* and 36*a*.

The provision of two sub-panels 28*a* and 28*b* allows for the practitioner to expose only a portion of the adhesive of the lower portion of the top layer at a time, thereby making application of the retractor/stabilizer to a patient's skin somewhat easier. As will become apparent below, the lower outer sub-panel 28*b* is the first panel from which the backing layer is removed, and is used to align the retractor/stabilizer on the patient. As such, it is the initial anchor point of the retractor/stabilizer on the patient and assists in the removal of the backing layer from the other panels (e.g., panels 28*a* and 26). If desired, the retractor could be formed with the two sub-panels formed as a single panel, such that the backing layer lower panel 28 is removed in one piece.

Grasping areas 40, 42, and 44 are formed by back cuts 40*a*, 42*a*, and 44*a*. The grasping area 40 is at the lower inner corner of the retractor/stabilizer; the grasping area 42 is at the junction between the upper edge 16*a* and outer side edge 16*b* of the retractor/stabilizer; and the grasping area 44 is defined by the shoulder 18 at the top inner portion of the retractor/stabilizer. In addition, the inguinal panel 20 also defines a grasping area. The cuts 22, 40*a*, 42*a*, and 44*a* separate the backing layers of these areas from the remaining backing layer of the retractor/stabilizer and enable the backing layer 12 to remain with the top layer 14 in each of the grasping areas 20, 40, 42, and 44 when the backing layer of the retractor/stabilizer body adjacent the grasping area is removed. As will become apparent below, the grasping areas will form areas in which the adhesive remains covered during application of the retractor/stabilizer 10 enabling the medical practitioner to hold on to the retractor/stabilizer without fear of his/her gloves becoming stuck to the top layer 14. The back cuts 22, 40*a*, 42*a* and 44*a* can be any desired shape or contour, so long as they define an area sufficiently large enough for the practitioner to grasp during use of the retractor/stabilizer without getting his/her gloves stuck to the adhesive side of the top layer.

Although the grasping areas 20, 40, 42 and 44 are described as being defined by back cuts and thus as being integral with the retractor/stabilizer, they could be formed by separate grasps or handles which are adhered to the top layer. These grasping areas or handles would accomplish the same function as the grasping areas which are integral with the retractor/stabilizer—they would allow for the technician to hold the top layer of the retractor/stabilizer without contacting the adhesive of the top layer after the backing layer has been removed.

Although the tabs and grasping areas are described as being graspable by practitioners (e.g., humans), the tabs and grasping areas could be designed to be grasped by robotic equipment (such as the da Vinci® robotic surgical system), to enable the retractor to be applied robotically.

Lastly, the retractor/stabilizer 10 can be provided with instructional indicia. Thus, the inguinal panel 20 and the lower inner grasping area 40 can each be printed with the phrase "Hold Here"; and the grasping areas 42 and 44 can each be printed with the phrase "Pull Here". Additionally, upper and lower arrows 50 and 52 are positioned on opposite ends for the word "MIDLINE". "MIDLINE" and the arrows 50,52 extend between the upper and lower edges of the retractor/stabilizer and are positioned toward the inner edge 16*c* of the retractor/stabilizer. The "MIDLINE" and the arrows 50,52 are provided to aid the practitioner when positioning the retractor/stabilizer on a patient, as will be described below. Finally an arrow 54 extends diagonally into the grasping area 44, to show the direction to pull the retractor/stabilizer during retraction/stabilization of a patient's panniculus. As seen, the arrow 54 is not collinear with the arrows 50,52. The arrow 54 is, however, generally parallel to the machine direction (noted by the arrow MD) of the retractor/stabilizer.

To apply the retractor/stabilizer 10 to a patient, the retractor/stabilizer, with the backing layer still applied to the top layer, is positioned over the patient's panniculus with the "MIDLINE" and the arrows 50,52 generally aligned with the midline of the patient (i.e., generally co-linear with the patient's sternum), and with the lower edge of the inguinal panel 20 positioned along or just above the patient's groin/inguinal crease or inguinal joint (i.e., the juncture between the patient's abdomen and groin). With the retractor/stabilizer generally positioned, the lower outer backing panel 28*b* is removed by grasping the A-tab 30 and pulling away from the top layer, thereby exposing the adhesive of the positioning portion of the top layer (i.e., area 28*b*). While holding the inguinal panel 20 the practitioner then applies the positioning portion of the top layer to the patient's abdomen, by smoothing the top layer over the patient's abdomen. The adhesive of the top layer in the exposed area secures the retractor/stabilizer to the patient. The retractor/stabilizer is positioned such that the lower outer edge of the top panel is proximate the patient's side, and the inguinal panel 20 is at the patient's inguinal crease (with the bottom edge of the inguinal panel being at or just above the inguinal crease). As can be appreciated, the backing layer remained with the inguinal panel 20 during the initial step of applying the retractor/stabilizer to the patient. This allowed for the practitioner to grasp the retractor proximate the exposed adhesive of the top layer without actually contacting the adhesive. Thus, the practitioner's gloves will not become adhered to the top layer.

With the retractor/stabilizer top layer initially secured and positioned on the patient, the inguinal panel 20 is hinged or folded up. Then the B-tab 32 is pulled to remove the backing layer from the top layer of the inguinal panel 20. The inguinal panel is then adhered to the patient by means of the adhesive on the inguinal panel top layer.

At this point, the retractor/stabilizer is folded back along cut line 31, and the C-tab is grasped to remove the backing panel 28*a* from the top layer to expose the remaining area of the bottom portion of the top layer. Holding the grasping area 40, the practitioner(s) apply this second portion of the top layer (i.e., area 28*a*) to the patient by smoothing the top layer across the patient's abdomen, and adhere this portion of the top layer to the patient with the adhesive on this section of the top layer. If desired, the cut line 31 (which divides the backing layer bottom panel 28 into two portions)

could be omitted, such that the bottom panel 28 of the backing layer is removed as one piece, rather than as two pieces.

After the lower portion of the top panel has been applied to the patient, the retractor/stabilizer 10 is bent or folded in a retrograde manner along the fold line 24, so that the upper panel 26 of the backing layer generally faces upwardly. One or both of the D-tabs 24 are then grasped to pull the upper panel 26 of the backing layer 12 away from the top layer 14. At this point, except for the protected grasping areas 40, 42, and 44, the backing panel 12 has been fully removed from the top layer. With the adhesive of the top layer exposed, the top layer should be held in tension (by holding the grasping areas 42 and 44) to prevent the top layer from touching itself and folding and adhering together. With the adhesive of the upper portion of the top layer exposed, the practitioner will hold the protected grasping areas 42 and 44 and pull the top layer upwardly (toward the head of the patient) and diagonally across the patient's midline. As noted above, the retractor/stabilizer 10 of FIG. 1 is a right side retractor/stabilizer. Thus, the inguinal panel/lower grasping area 20 is located proximate the right hip. The practitioner thus pulls diagonally (holding and pulling the grasping area 16) toward the left shoulder to adhere the top inner portion (i.e., proximate the grasping area 44) to the left of the patient's xiphoid process or area or proximate the patient's left breast. By pulling on the top layer in this manner, the top layer is used to retract the panniculus both in a cephalad and angular (cross midline) direction towards the left shoulder (with respect to the retractor of FIG. 1). With the approximately one-half (or with one side) of the panniculus retracted, the top layer 14 is held in tension (again, while holding on to the protected grasping areas) and smoothed over the patient's skin with the target of adhering the top inner portion of the body 16 below the opposite (left) breast or to the opposite side of the patient's xiphoid process or area, as just noted. Thus the retractor/stabilizer 10 is pulled from the hip towards the opposite shoulder, and anchored proximate the breast or xiphoid area on the opposite side of the patient from the inguinal panel. The retraction of the panniculus occurs in two directions (i.e., both vertically and horizontally) across the patient's torso, resulting in an axis of retraction that is generally parallel to a line extending between the patient's hip and opposite shoulder. This retraction can be described as a bidirectional retraction. The angle of the retraction is such that the upper anchor point is about 5° to about 45° across the patient's midline, and preferably between about 10° and about 20° across the patient's midline. Stated differently, the direction of retraction defines an angle of between about 5° and about 45° (and preferably between about 10° to about 20°) with the patient's midline.

The portion of the panniculus to which the top layer 14 has been applied will now be retracted and stabilized, and the abdominal exposure in the retracted portion of the panniculus should be at least 90°, and can be up to 180°. As can be appreciated, the top layer is adhered to the patient's skin substantially over the entire adhesive coated surface of the top layer. As long as the top layer 14 is held in tension, should there be an error in application of the retractor/stabilizer, the retractor/stabilizer can be partially removed from the patient and repositioned and reapplied. Once the retractor/stabilizer is fully adhered to the patient, the panniculus is stable and retracted.

The reader may have noticed that the tabs 30, 32, 34, and 36 (FIG. 1) are labeled "A", "B", "C", and "D" and that the tabs are used in alphabetical order when removing the backing panels from the top layer of the retractor/stabilizer. This labeling of the tabs facilitates application of the retractor/stabilizer by noting the order in which the backing layer panels are to be removed and the order in which the top layer 14 is to be applied to the patient's skin, thus producing a delivery system/process for the retractor/stabilizer.

With the top layer of the retractor/stabilizer 10 in place, the top layer 14 will hold the retracted portion of the patient's panniculus in position without any further effort required by the practitioners. The shape and flexibility of the retractor/stabilizer conforms to the shape of the patient and lends itself to corrugation or folding of redundant or adipose tissue which forms the panniculus. The retractor/stabilizer 10 thus effectively retracts a portion of the patient's anatomy to a more natural anatomical configuration when it redistributes and supports the excessive and/or redundant tissue (in this example, the patient's panniculus) and orients to internal anatomical landmarks.

The top layer 14 of the retractor/stabilizer is designed such that the machine direction of the top layer runs generally diagonally relative to a vertical axis of the retractor/stabilizer, and generally parallel to the direction in which the top layer 14 is pulled during application of the retractor/stabilizer to the patient. This is shown by the arrow MD in FIG. 1. The machine direction can define an angle of about 35° to about 45° with respect to a line defined by the arrows 50,52. Stated differently, the machine direction of the top layer runs diagonally, or extends generally from bottom outer edge to top inner edge (or vice-versa) of the retractor/stabilizer. This provides for an increase in tensile strength of the top layer in the direction of pull and the direction of tensile forces applied to the retractor/stabilizer after application to the patient.

The retractor/stabilizer 10 is self-supporting and self-contained. There is no need for straps, hook and loop, belts, buckles, adhesive pads or strips, etc. that are secured to the patient, operating room gurney or patient examining table, and practitioners do not need to hold the panniculus in the retracted position after application of the retractor/stabilizer. The only support required for the use of the retractor/stabilizer is the patient him/herself. Thus, use of the retractor/stabilizer 10 will essentially eliminate the potential for fatigue and/or injury caused to practitioners holding a patient's panniculus in place. Further, the retractor/stabilizer can be applied quickly (often in less than one minute). This is substantially faster than current strap-based retractors can be applied. The fact that the retractor/stabilizer can be applied quickly and is self-supporting benefits the patient, in that the patient is likely to be less embarrassed. Further, the retractor/stabilizer, when applied, enables personnel to shift and lift, displace, reposition and then hold in place excessive and/or redundant tissue.

The angle at which the retractor/stabilizer is applied relative to the patient's midline may vary depending on the size of the patient's panniculus and the target site on the patient that is desired to be exposed. For example, if the target site is the patient's side (for example, in a hip replacement), then the practitioner may apply the retractor at more of an angle than, for example, if the target area is closer to the midline (for example, in a hernia repair). The angle of application of the retractor relative to the patient's midline can thus be from about 5° to about 45°, and preferably about 5° to about 20°.

Previously, if practitioners did not use a retractor/stabilizer which included straps which adhered to the bed, they may have used tape. The use of tape (i.e., medical tape or even duct tape) is noisy and thus disruptive to the surgical team. Further, the tape may not be sterile, as may be required. And, the practitioners' gloves may stick to the adhesive of the tape. The retractor/stabilizer 10, which can be sterilized, eliminates these issues.

The retractor/stabilizer can be provided in different sizes (in both side-to-side width and top-to-bottom length) so that the retractor/stabilizer can be used with a Grade I panniculus (which extends to the pubic hairline) to a Grade V panniculus (which can extend beyond the patient's knees). The retractor/stabilizer is formed by a die cutting process, typically from a web of the two-ply material (although the material can have 3 or more plies), and, the size of the retractor/stabilizer is dictated by the capability of the equipment used to form the retractor/stabilizer.

When the medical procedure has been completed, removal of the retractor/stabilizer 10 is simple as well. The practitioners take hold of the protected grasp areas and gently elevate the retractor/stabilizer to separate the retractor/stabilizer from the patient's skin. During removal, the patient's skin should be supported or pushed away from the retractor/stabilizer, and the removal should be accomplished in slow, short, 2-3 inch segments at a time. Upon removal, the retractor/stabilizer should be disposed of in accordance with the relevant regulations. The use of the retractor/stabilizer does not lead to any residual effects to the patient. Nonetheless, the patient's skin should be assessed for any adverse reactions.

The retractor/stabilizer anchors the weight of the patient's panniculus to the patient's xiphoid area or below the patient's breast on a side of the sternum opposite the inguinal panel. Thus, if the inguinal panel is on the patient's left side, the anchor point for the top inner portion of the retractor/stabilizer is the right side of the sternum. Conversely, if the inguinal panel is on the patient's right side, the anchor point for the top inner portion of the retractor/stabilizer is the left side of the sternum. As noted above, the retractor/stabilizer shown in FIG. 1 is a patient "right-side" retractor/stabilizer. A patient "left-side" retractor/stabilizer would be a mirror image of the "right-side" retractor/stabilizer.

When the practitioners release the panniculus after application of the retractor/stabilizer 10 to the patient, the panniculus relaxes slightly. Because the bottom of the retractor/stabilizer is secured to the panniculus below the horizon of the panniculus (i.e., toward the bottom of the panniculus or at the radius of the panniculus), relaxation of the panniculus will place the retractor/stabilizer top layer in tension, and it will pull against the patient's xiphoid or chest area. Thus, initially, the retractor/stabilizer is a flexible, conformable retractor/stabilizer that operates beginning in a relaxed state and uses tension to reposition, replace, and manipulate tissue, and in particular, excessive and/or redundant tissue. Upon application of the retractor/stabilizer, the underlying tissue is in compression, and the patient's excessive and/or redundant tissue may end up in folds or corrugations. When the panniculus is retracted, using the retractor/stabilizer, the thoracic cavity is not compressed. Rather, the tensile forces in play have been found to reduce pressure on the patient's chest (thoracic) cavity. The weight of the panniculus acts as a counterweight. When the retractor/stabilizer is anchored proximal to the xiphoid, a horizontal/planar sheer force assists in the expansion of the diaphragm when the panniculus relaxes away from the xiphoid, thereby assisting with tidal volume (i.e., lung volume representing the volume of air displaced between inhalation and exhalation). It has been observed that by removing the pressure which is exerted by the panniculus on the chest cavity (a pressure which remains with other current methods), the anesthesiologist is provided with better access to the patient's airways. This makes intubation of the patient easier and aids the control of the patient's breathing during surgery easier. This effect has also been referred to as thoracic dilation and diaphragmatic excursion. This diaphragmatic excursion may be useful in other patients as well.

Figure 3:
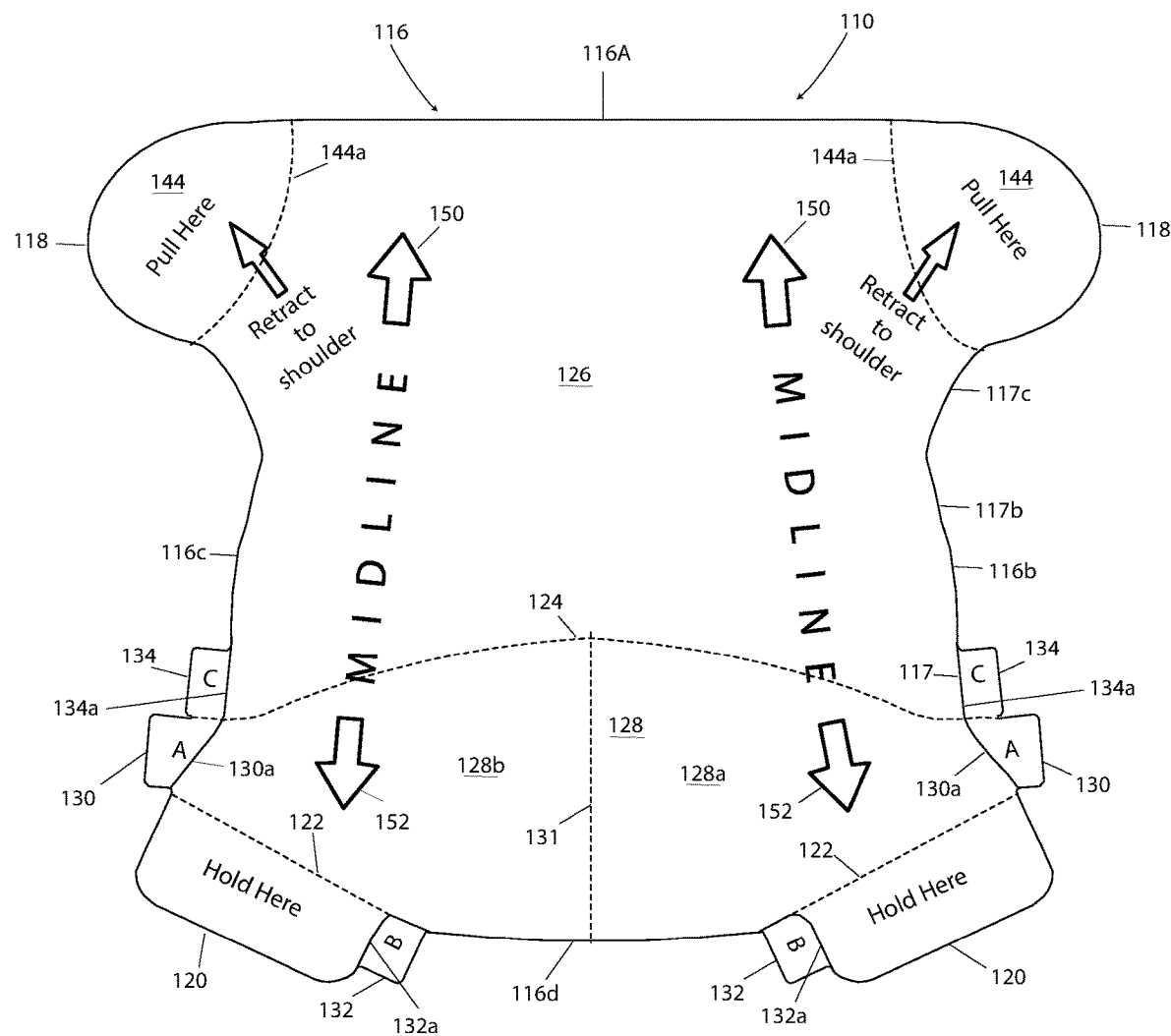
FIG. 3 is a "universal" embodiment of the retractor/stabilizer, which can be applied to either the left or right side of the patient.

The retractor/stabilizer 10, as noted, is side-dependent. That is, there is a right side retractor (shown in FIG. 1) and a left side retractor (which is a mirror image of the retractor 10 of FIG. 1). A universal retractor/stabilizer 110 is shown in FIG. 3 which can be applied to either the right side or left side of the patient. The universal retractor/stabilizer 110 defines a body 116 having a top edge 116a, side edges 116b,c, and a bottom edge 116d. Unlike the retractor 10, the side edges 116b,c of the retractor/stabilizer 110 are mirror images of each other. Each includes a lower inwardly sloping portion 117a at the bottom of the body 116, a middle generally vertical portion 117b extending upwardly from the portion 117a, and an upper outwardly sloping portion 117c extending from the middle portion 117b. The upper portion 117c of the side edges 116b,c merges into shoulder shoulders 118 that extend from the side edges 116b,c. The retractor/stabilizer 110 further includes opposed inguinal panels/lower grasping areas 120 at the bottom of each side edge 116b,c. The backing layer of the inguinal panels 120 are separated from the backing layer of the body 116 by back cuts 122.

As with the retractor/stabilizer 10, the retractor/stabilizer 110 includes a back cut 124 which separates the backing layer of the body 116 into an upper portion 126 and a lower portion 128. In addition, a vertical back cut 131, which bisects the bottom edge 116d, divides the bottom portion 128 into left and right portions 128a,b.

The retractor/stabilizer includes a tab associated with each backing panel. An A-tab 130 is associated with each lower portion subpanel 128a,b and is positioned along the bottom portion 117a of the body side edges 116b,c between the cut line 124 an and the bottom edge of the body; a B-tab 132 is associated with each of the inguinal panels 120, and positioned along an inner edge (spaced from the body sided edges 116b,c) of the panels; and two C-tabs 134 are associated with the body upper panel 126, and are positioned along the side edges 116b,c above the A-tabs. The top layer of the A- and C-tabs are separated from the upper layer of the body by face cuts 130a, 134a; and the top layers of the B-tabs 132 are separated from the upper layer of the inguinal panels 120 by face cuts 132a.

The inguinal panels 120 define lower grasping areas for the retractor/stabilizer. In addition, the shoulders 118 define grasping areas 144, and the body 116 includes back cuts 144a to separate the backing of the shoulders 118 from the backing of the body 116.

As noted, the retractor/stabilizer 110 is a "universal" retractor/stabilizer, and thus can be used with either the left or right side of the patient. The retractor/stabilizer thus includes a MIDLINE notation and directional arrows 150, 152 extending generally parallel to the side edge portions 117b and set inwardly from each of the side edges 116b,c.

In the retractor/stabilizer 10, the machine direction runs diagonally, generally parallel to a line running from the inguinal panel 20 to the shoulder 18. If the machine direction of the retractor 110 were to run diagonally from one inguinal panel 120 to the opposite shoulder 118, the top panel could have a greater elongation or stretch factor in one diagonal direction than the other. For example, the top layer could stretch more along a right-left diagonal if the machine direction ran left-right diagonal. Thus, so that the retractor/ stabilizer 110 have generally the same elongation/stretch factor regardless of its use as a right or left side retractor, the machine direction can run either widthwise (i.e., from side-to-side) or lengthwise (i.e., from top to bottom). Whether the machine direction for the retractor 110 runs widthwise or lengthwise depends on the desired effect. If the machine direction runs widthwise, the retractor will have more stretch than if the machine direction runs lengthwise. Conversely, if the machine runs lengthwise, the retractor will have greater tensile strength (in a top-to-bottom direction) than if the machine direction runs widthwise.

Use of the retractor/stabilizer 110 is generally similar to use of the retractor 10. Initially, the retractor/stabilizer 110 is positioned over the patient's body with the appropriate (right or left) MIDLINE notation aligned with the patient's midline. The appropriate (right or left) lower panel section 128*a,b* is then removed to adhere the retractor/stabilizer to the patient and position the retractor/stabilizer to the patient. Thus, if the retractor/stabilizer is being used as a left side retractor/stabilizer, the left sub-panel 128*a* is removed first. Conversely, if the retractor/stabilizer is being used as a right side retractor/stabilizer, the right-side sub-panel 128*b* is removed first. The retractor/stabilizer is then folded/bent generally about the cut line 131, and the other sub-panel is removed, to complete application of the bottom portion of the retractor/stabilizer top layer to the patient. The retractor/stabilizer is then bent retrograde and the upper panel 126 is removed. The retractor/stabilizer is then pulled diagonally in a cephalad direction, to retract the panniculus and anchor the retracted panniculus to the xiphoid area on the opposite side of the patient's midline.

If the retractor/stabilizer 10, 110 is to be used during a surgical procedure, then the top layer is preferably formed from a fluid impervious material. Further, the top layer can be formed from a material which can be incised (i.e., cut). The retractor/stabilizer can also be used for wound care, for example, to keep the panniculus raised to facilitate healing of an abdominal incision or other abdominal wound, such as disclosed in our WO2016/122892 entitled "Wound Exposure Device For Use With Patients Having Excessive And/Or Redundant Tissue And Method Of Use", which is incorporated herein by reference. In such a situation, the top layer 14 is preferably made from a breathable material through which vapor can pass. For example, the top layer could be made from a polyurethane, cloth (made from man-made or natural fibers), paper, silicone, etc. Further, although the top layer is preferably clear (i.e., transparent), it can be translucent or even opaque. Additionally, the top layer could be colored if desired.

Figure 4:
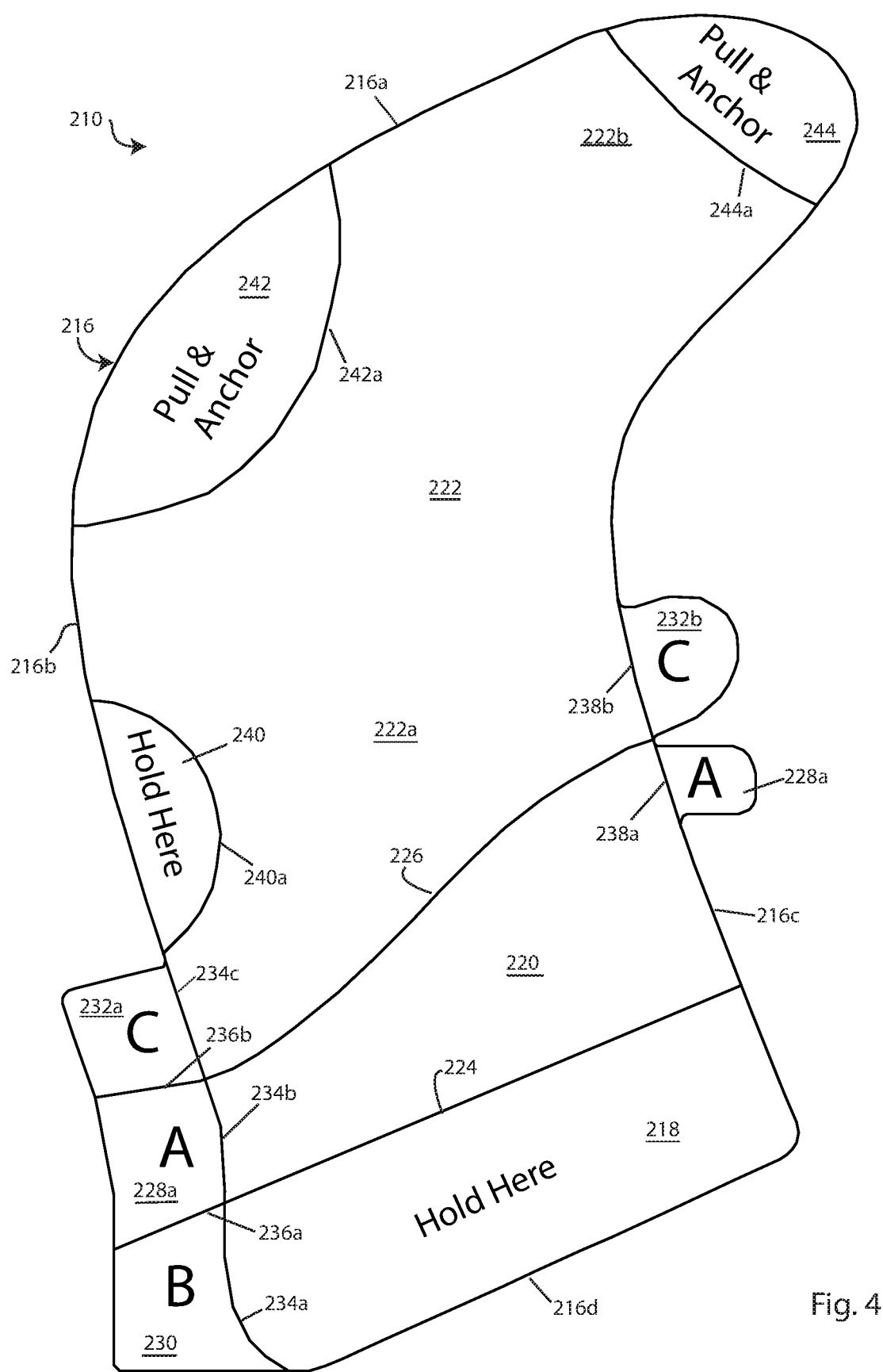
FIG. 4 is a plan view of a second, alternative, configuration of the retractor, wherein the retractor resembles a sock.

Another single side retractor/stabilizer 210 is shown in FIG. 4. Like the retractor/stabilizer 10, the retractor/stabilizer 210 can be formed as a left side or right side retractor/stabilizer, with the right and left retractor/stabilizers being mirror images of each other. The retractor/stabilizer 210 can be narrower (from side-to-side) and thus can be used in thinner or narrower areas, such as retracting excess tissue on a patient's side.

The retractor/stabilizer 210 comprises a body 216 having an upper edge 216*a*, an outer edge 216*b*, an inner edge 216*c*, and a bottom edge 216*d*. The edges are shaped such that the retractor/stabilizer is shaped like an upside-down sock. The body 216 of the retractor/stabilizer 210 is divided into a bottom grasping area or panel 218, a positioning area 220, and an upper area 222. In the right sided retractor/stabilizer 210 shown in FIG. 4, the upper area 222 has a main portion 222*a* which extends upwardly from the positioning area 220 and an anchoring portion 222*b* which extends upwardly and to the right in the embodiment shown. In a left sided retractor/stabilizer, the anchoring portion 222*b* would extend upwardly and to the left. This anchoring portion corresponds to the "foot" of the "sock" in the "sock"-shaped retractor/stabilizer.

The backing of the grasping area/panel 218 is separated from the backing of the positioning portion 220 by a back cut 224; and the backing of the positioning portion 220 is separated from the backing of the main portion 222 by a back cut 226. Tabs are associated with each area/portion 218, 220 and 222, so that the backing can be removed from the three areas/portions independently. A-tabs 228*a,b* are associated with the positioning panel 220, and extend from the inner and outer edges 216*b* and 216*c*, respectively. A B-tab 230 is associated with the grasping panel 218, and extends from the inner edge 216*b* of the body 216. Lastly, C-tabs 232*a,b* are associated with the main panel 222, and extend from the inner and outer edges 216*b* and 216*c*, respectively. The A, B and C tabs 228*a*, 230 and 232*a* extending from the inner edge 216*b* of the body 216 are adjacent each other, with their junction with the body 216 being defined by top cuts 234*a-c*, and with the tabs being separated from each other by full cuts 236*a,b*. The A- and C-tabs 228*b* and 232*b*, extending from the outer edge 216*c* have inner ends defined by top cuts 238*a,b*. Although only a single B-tab 230 is shown, the retractor/stabilizer 210 could be provided with a second B-tab, which could extend from the bottom edge 216*d* or the outer edge 216*c*.

The retractor/stabilizer 210 further includes a first grasping area 240 on the outer edge 216*b* of the body above the C-tab 232*a*. Another grasping area 242, labeled first "pull and anchor," is formed at the "heel" of the sock-shaped retractor/stabilizer 210 (i.e., at the curved junction of the outer edge 216*b* and the top edge 216*a*). Lastly, a further grasping area 244, also labeled "pull and anchor," is formed at the "toe" of the sock-shaped retractor/stabilizer 210 (i.e., at the curved end of the anchoring portion 222*b* of the body 216. The grasping areas 240, 242 and 244 are defined by bottom cuts 240*a*, 242*a*, and 244*a*, which are shaped such that when the backing is removed from the body 216, the backing remains with the top layer in these areas. Hence, the bottom cuts 240*a*, 242*a*, and 244*a* all begin and end at an edge of the body 216. As seen, the grasping area 244 is horizontally spaced from the outer edge 216*c* of the retractor/stabilizer. This facilitates pulling/stretching the retractor in a cross-midline direction when the retractor/stabilizer is applied to a patient.

In use, the retractor/stabilizer 210 is generally positioned relative to the patient over the tissue to be retracted/stabilized. If being used to retract the patient's panniculus, the retractor/stabilizer is positioned so that the bottom edge is above the patient's inguinal crease. With the retractor/stabilizer generally positioned relative to the patient, one, or both, of the A-tabs 228*a,b* are pulled to remove the backing layer in the positioning portion 220 of the body 216. With the backing layer in the positioning portion removed, the retractor is applied to the patient on the tissue to be retracted (i.e., is applied to the panniculus). During this step, the medical personnel can hold the retractor/stabilizer body 216 in the grasping area 218 at the bottom of the body and anywhere on the main body portion 222. Once the retractor has initially been adhered to the patient, the B-tab 230 can be pulled to remove the backing layer from the grasping area 218, and the top layer in the grasping area 218 can be smoothed over the patient's skin. In the example of a panniculus, the retractor/stabilizer is positioned such that the panel 218 is applied to the horizon of the patient's panniculus. The personnel then pull one, or both, of the C-tabs 232a,b to remove the backing layer from the body main portion 222, except for in the grasping areas 240, 242, and 244. In these three grasping areas, the backing layer remains with the top layer, to enable personnel to handle the retractor without contacting the adhesive of the top layer. The personnel pull the retractor in a retracting direction (generally in a cephalad direction) to retract the excess tissue. Once retracted, the top of the anchoring portion 222b of the retractor is adhered to the patient at an anchor point on the patient. If desired, the three areas 240, 242 and 244 can be provided with tabs, so that the backing layer can be removed from the top layer in these areas.

Figure 5:
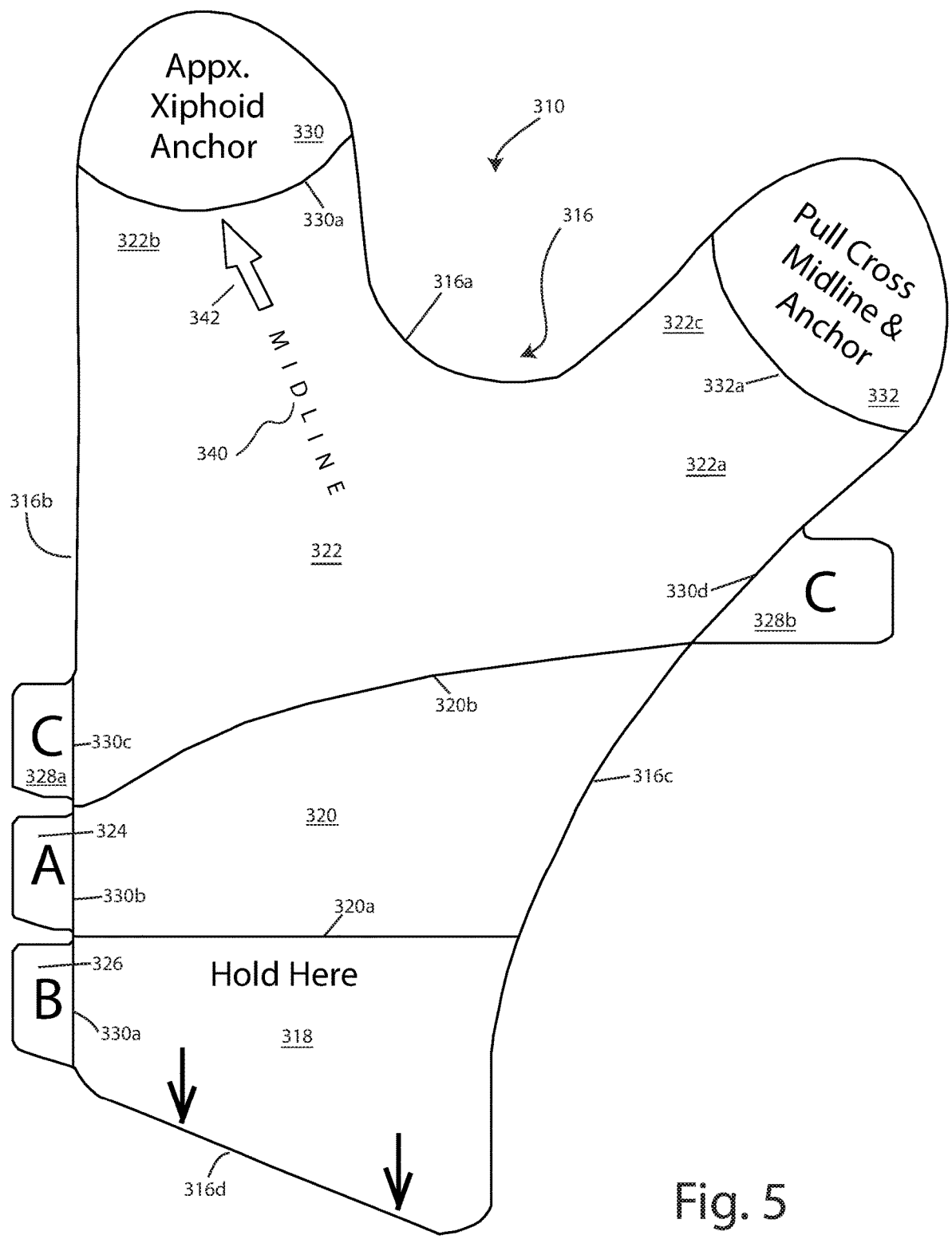
FIG. 5 is a plan view of a further alternative configuration for the retractor in which the retractor is generally Y-shaped.

A generally Y-shaped retractor/stabilizer 310 is shown in FIG. 5. Like the retractor/stabilizer 10 and 210, the retractor/stabilizer 310 can be formed as a left side or right side retractor/stabilizer, with the right and left retractor/stabilizers being mirror images of each other. The retractor/stabilizer 310 includes a body 316 having a generally U-shaped top edge 316a, a generally straight outer side edge 316b, an outwardly curved inner side edge 316c, and a downwardly sloping bottom edge 316d. The body 316 is divided into three sections—a bottom grasping area/panel 318, a positioning section 320, and a main section 322. The positioning section 320 is separated from the grasping area/panel 318 and the main section 322 by bottom cuts 320a,b. The main section 322 includes a main body portion 322a, a xiphoid anchor lobe 322b and a cross-midline anchor lobe 322c. The xiphoid anchor lobe is defined by the outer side edge 316b and a portion of the top edge 316a, while the cross-midline anchor lobe is defined by the inner side edge 316c and a portion of the edge 316a of the body 316.

At least one tab is associated with the bottom layer of each section, so that the bottom layer of the three sections can be removed independently of each other. Thus, an A-tab 324 is provided for the positioning section 320; a B-tab 326 is provided for the grasping area/panel 318; and two C-tabs 328a,b are provided for the main section 322. The tabs 324, 326, and 328a extend from the outer side edge 316b and the C-tab 328b extends from the inner side edge 316c. The tabs are separated from the body 316 of the retractor/stabilizer by top cuts 330a-d, all of which are co-linear with, or part of, the side edges 316b,c from which the tabs extend. Although two C-tabs are provided, the retractor/stabilizer could be provided with just one C-tab. Alternatively, the retractor/stabilizer could be provided with two A-tabs and/or two B-tabs.

Additionally, the retractor/stabilizer includes two upper grasping areas 330,332 at the ends of the xiphoid anchor lobe 322b and the cross-midline anchor lobe 322c. These grasping areas are both defined by bottom cuts 330a and 332a, respectively, such that when the backing layer 12 is removed from the main area 322, the backing area will remain with the grasping areas 330, 332. If desired, additional tabs could be provided for each of these hold areas to remove the backing layer 12.

Lastly, the retractor/stabilizer 310 is provided with a midline indicator 340 and an associated arrow 342. As seen, the grasping area 332 is horizontally offset from the outer edge 316c, and an axis of the lobe 322b defines an angle α of about 50° to about 90° with an axis of the midline indicator arrow 342.

In use, the retractor/stabilizer 310 is generally positioned relative to the patient over the tissue to be retracted/stabilized, with the bottom edge 316d of the retractor/stabilizer body 316 being above and generally parallel to the patient's inguinal crease. In this position, the midline indicator 340 and arrow 342 should be generally aligned with the patient's midline (i.e., generally co-linear with the patient's sternum). The A-tab 324 is pulled to remove the backing layer in the positioning portion 320 of the body 316. With the backing layer in this portion removed, the retractor is applied to the patient. In this step, the medical personnel can hold the body 316 by the grasping area 318 at the bottom of the body and anywhere on the main body portion 322. Once the retractor has initially been adhered to the patient, the B-tab 326 can be pulled to remove the backing layer from the grasping area 318, and the top layer in the grasping area 318 can be smoothed over the skin of the tissue to be retracted (e.g., the patient's panniculus). The personnel then pull one, or both, of the C-tabs 338a,b to remove the backing layer from the body main portion 322, leaving the backing layer in the grasping areas 330, 332 to enable personnel to handle the retractor without contacting the adhesive of the top layer. The personnel pull the retractor in a retracting direction (generally in a cephalad direction) and across the midline to retract the excess tissue. Once retracted, the top of the xiphoid anchoring portion 322b of the retractor is adhered to the patient at an anchor point proximate the patient's xiphoid area. Subsequently, the cross-midline lobe 322a is stretched in a direction away from the patient's midline, to further retract the excess tissue to, with the retractor of FIG. 5, the patient's left, and anchor the cross-midline anchor lobe to a second point on the patient's body, for example, proximate or below the patient's shoulder. If desired, as noted above, the grasping areas 330, 332 can be provided with tabs, so that the backing layer can be removed from the top layer in these areas. If desired, the cross-midline anchor lobe can be positioned and anchored before the xiphoid anchor lobe is adhered to the patient.

Figure 6:
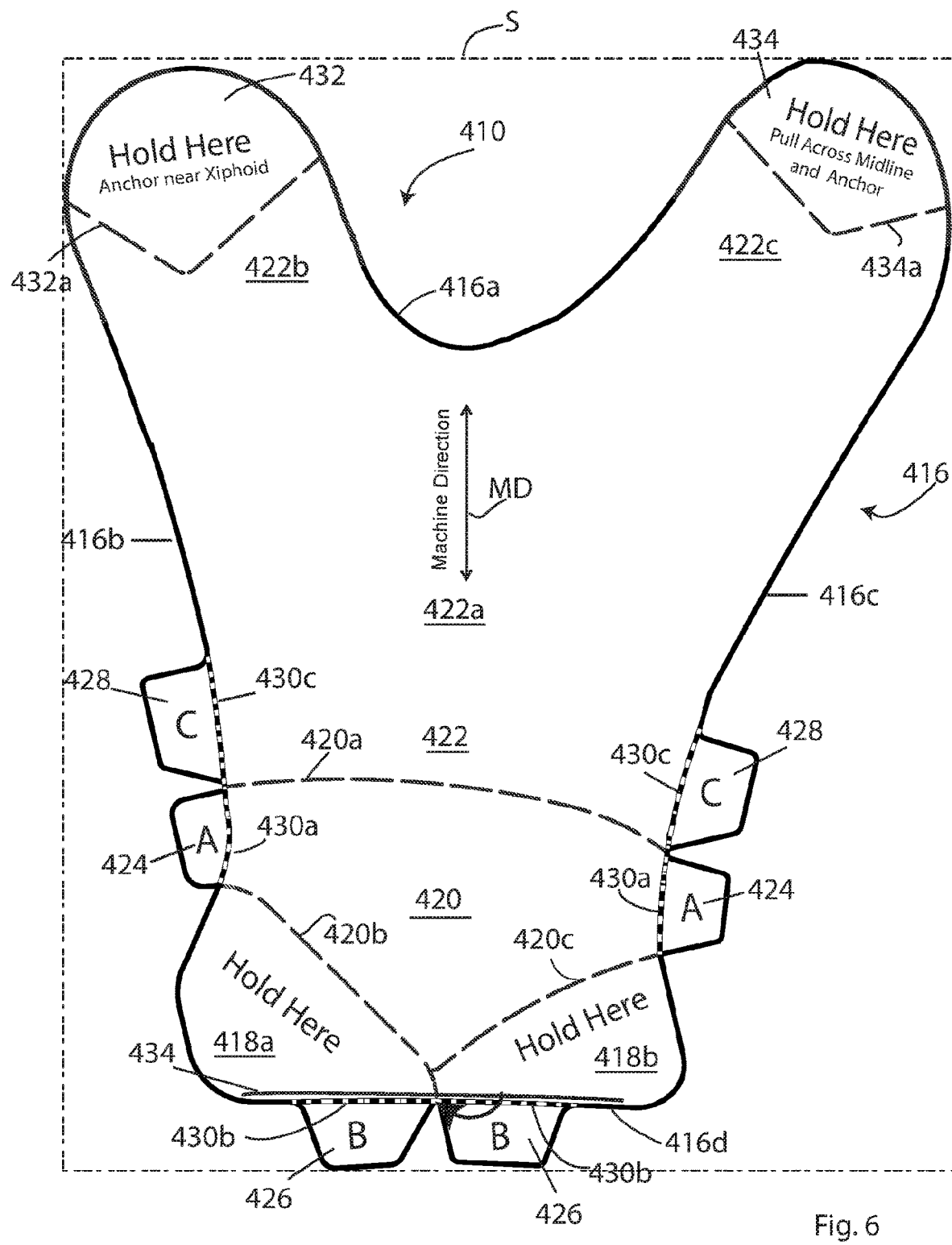
FIG. 6 is a plane view of another generally Y-shaped configuration for the retractor.

A second generally Y-shaped retractor/stabilizer 410 is shown in FIG. 6. Like the retractor/stabilizers 10, 210, and 310, the retractor/stabilizer can be formed as a left side or right side retractor/stabilizer, with the right and left retractor/stabilizers being mirror images of each other. The retractor 410 is shown positioned on a sheet S of material from which the retractor/stabilizer is cut. Preferably, the retractor/stabilizer 410 is cut from sheet S with the machine direction MD extending from the top-to-bottom direction of the retractor 410.

Unlike the Y-shaped retractor 310, the retractor 410 is generally symmetrical about an axis parallel to the machine direction. The retractor/stabilizer 410 includes a body 416 having a generally U-shaped top edge 416a, an inner side edge 416b, an outer side edge 416c, and a bottom edge 416d. As seen, the side edges both extend generally inwardly from the bottom corners of the body for a short distance to define a "waist", and then extend outwardly from the "waist". The "waist" points on the two sides of the retractor/stabilizer body are not level with each other, and thus, a line extending between the two points would slope downwardly from the left side of the retractor/stabilizer to its right side (with reference to FIG. 6). The body 416 is divided into three sections—a bottom section comprising two grasping areas 418a and 418b, a positioning section 420, and a main section 422. The positioning section 420 is separated from the main section by an upwardly curving bottom cut 420a, and is separated from the two grasping areas 418a,b by a pair of downwardly and inwardly sloped bottom cuts 420b,c. The bottom cut 420b extends from about the "waist" at the edge 416b to the approximate center of the bottom edge 416d. The bottom cut 420c extends from about the "waist" at the edge 416c inwardly and downwardly to intersect the bottom cut 420b slightly above the approximate mid-point of the bottom edge 416d of the body 416. The upper bottom cut 420a intersects the side edges 416b,c above the bottom cuts 420b,c. Thus, the positioning section 420 defines an upside down, generally symmetrical pentagon having squat side edges defined by the side edges 41 6b,c of the body 416, a base defined by the bottom cut 420a, and a triangular portion defined by the bottom cuts 420b,c. The main section 422 includes a main body portion 422a, a xiphoid anchor lobe 422b and a cross-midline anchor lobe 422c. The xiphoid anchor lobe is defined by the inner side edge 416b and a portion of the top edge 416a, while the cross-midline anchor lobe is defined by the outer side edge 416c and a portion of the edge 416a of the body 416.

At least one tab is associated with the bottom layer of each section. Thus, a pair of A-tabs 424 is provided for the positioning section 420; a B-tab 426 is provided for each grasping area 418a,b; and a pair of C-tabs 328 is provided for the main section 322. The A- and C-tabs 424 and 428 extend from the side edges 316b,c on opposite sides of the bottom cut 420a. The B-tabs extend downwardly from the bottom edge 416d on opposite sides of the intersection of the cut 420b with the bottom edge 416d. As seen, the B-tabs 426, in combination, define an upside-down "V." The tabs 424, 426, and 428 are separated from the body 416 of the retractor/stabilizer by top cuts 430a-c, all of which are co-linear with, or part of, the edge from which the respective tab extends.

Lastly, the retractor/stabilizer includes two more grasping areas 432 and 434 at the ends of the xiphoid anchor lobe 422b and the cross-midline anchor lobe 422c, respectively. These hold areas are both defined by generally V-shaped bottom cuts 432a and 434a, respectively, such that when the backing layer 12 is removed from the main area 422, the backing area will remain with the grasping areas 432 and 434. If desired, additional tabs could be provided for each of these grapsing areas to remove the backing layer 12. An axis of the cross-midline anchor lobe defines an angle B of about 25° to about 50° with the machine direction, and an angle C of about 45° to about 70° with an axis of the xiphoid anchor lobe. The grasping area 434, as seen, is off set from the edge 416c (in the area of the positioning section 420), and thus facilitates pulling/stretching of the retractor cross-midline during application of the retractor to a patient.

The application of this retractor is substantially the same as for the retractor 310, and thus its application to a patient need not be explained. However, it is noted that the retractor/stabilizer includes a line 434 printed on the body slightly above, and parallel to, the bottom edge 416d of the body. The line 434 shows the profile, or the outline of the retractor/stabilizer top layer after the pull tabs have been utilized to remove the bottom layer 12 from the top layer 14 of the retractor/stabilizer. It is also a printed reference line which, in use shows the true bottom line of the retractor/stabilizer after application to the patient. The line 434 additionally serves as a guide to place the retractor above the inguinal crease.

As noted above, any of the retractor/stabilizers can be provided with indicators to monitor and inform of, for example, changes in elongation and/or stretch of the retractor/stabilizer. Additionally, The retractor/stabilizer may include one or more sensor boards (including sensors) that monitors/collect and transmit data relative to ambient and physiological aspects of the patient's wound. For example, such sensors can monitor/detect the presence of biological (i.e., bacterial or viral) agents, physiological data (i.e., blood pressure, skin temperature at the incision site, heart rate), or concentrations of specific chemicals, vapors or gases (such as $H_2O$, $O_2$ or $CO_2$). Such sensors could also monitor the stretch/elongation of the retractor/stabilizer. Sensors and indicators which monitor elongation and/or stretch of the retractor/stabilizer can be placed anywhere on the retractor/stabilizer, and be used to monitor the stretch/elongation of the retractor/stabilizer in a direction of the tension of the retractor/stabilizer (i.e., in a direction generally parallel to the arrows 50,52). This stretch direction could be, but is not necessarily, parallel to the machine direction of the retractor/stabilizer.

An indicator/sensor which monitors or responds to elongation/stretch will provide an indication if the retractor/stabilizer exceeds more than a predetermined amount (percentage) of its maximum elongation/stretch. As can be appreciated, this can be beneficial during application of the retractor/stabilizer to the patient. Additionally, if the retractor/stabilizer is to be worn long term (i.e., for days, or even weeks) as was noted above, an stretch/elongation indicator/sensor can determine if undue stresses are placed on the retractor/stabilizer which could affect the ability of the retractor/stabilizer to maintain the panniculus in a retracted position (and off a wound).

An indicator/sensor which monitors or measures ambient and physiological aspects of the patient's wound are preferably positioned on the retractor/stabilizer so as to be proximate the incision site. These indicators/sensors can be applied to the retractor/stabilizer after application of the retractor/stabilizer to the patient, or the retractor/stabilizer can be supplied with the sensor(s) already positioned on the retractor/stabilizer. Such an indicator/sensor would provide a notification if the monitored parameter exceeds or falls below a predetermined threshold. This can be relevant during a procedure. However, it can be more relevant if the retractor/stabilizer is worn long term. A rise in temperature or an increase in bacterial or viral activity can denote the infection has set in, or is setting in, at or around the incision site. A drop in $O_2$ levels or an increase in $H_2O$ levels could indicate that the incision site is not receiving enough air.

The stretch indicator can be mechanical, or as noted, incorporated in an electrical sensor. The sensor used in association with wound care is positioned to collect/monitor/assemble data relative to ambient conditions and physiological aspects of the patient and transmit the data to a receiver. The receiver can be a dedicated receiver or an application (app) on a personal device. Data collected is evaluated by the receiver to monitor ambient conditions at the incision site to determine the conditions at the incision site (wound).

If sensors are used, the retractor/stabilizer will be provided with a power source for the sensors. The sensors are wired or wireless and can be integrated into the retractor/stabilizer or placed in close proximity to the target site (either prior to or after the retractor/stabilizer has been applied the patient). The signal from the sensor will be received by a monitor/receiver which will interpret the signal. The monitor can, for example, be a personal device provided with an application (app) adapted to receive the signal from the sensor via, for example, blue tooth connectivity, or any other type of wireless connectivity. Alternatively, the monitor can be a dedicated monitor. The monitor can issue a visual, tactile (vibratory) or audible alert if the monitored parameter falls out of predetermined bounds. In addition to notifying the patient of an out of bounds parameter, the monitor can send a signal to a practitioner, so that the practitioner can receive warning of the out-of-bound condition. The practitioner can then take appropriate corrective actions as may be necessary.

We have found that the retractor/stabilizers 10, 110, 210, 310, 410 displace excessive and/or redundant tissues, thereby minimizing and reducing the distance between the dermis and the target area (i.e., surgical site) to which the retractor/stabilizer is adhered. This displacement of the excessive and/or redundant tissue greatly facilitates imaging. In obese patients, there is a layer of fatty or adipose tissue that will typically overlie the imaging target (such as an organ, joint, artery/vein, etc.). If the excessive and/or redundant tissue is not displaced, the imaging energy (i.e., ultrasound) will need to pass through the excessive and/or redundant tissue to reach the imaging target. In order to obtain a good image of the imaging target through the excessive and/or redundant tissue, the imaging power or energy, for example, of the ultrasound signal needs to be increased. When retracting and stabilizing a patient's excessive and/or redundant tissue using the retractor/stabilizer (with or without an extension member), the excessive and/or redundant tissue between the imaging target and the patient's skin is moved by the repositioning of the excessive and/or redundant tissue. This effectively reduces the distance that imaging energy (such as ultrasound energy) must travel, and thus, the need to use a higher energy power is mooted. Further, because the imaging energy travels through less tissue, the image is more defined. The reduced distance (i.e., the retraction/displacement of the excessive and/or redundant tissue) also facilitates vascular access. For example, during vascular access or nerve block procedures in the femoral region, use of an ultrasound guided needle is required to access either the femoral artery or nerve. Use of the retractor/stabilizer reduces the penetration distance required because the distance between the dermis and target site is reduced. Vascular access in the groin, for example, can be used to insert stents. Easier (or enhanced) vascular access in other regions of the body facilitates nerve block and pain management. Use of the retractor/stabilizer during radiation therapy, for example, for ovarian cancer, allows for a reduction in the amount of energy needed to treat the cancer because the distance between the skin and the target tissue is shorter. That is, less energy is required to treat the target because redundant tissue is retracted from the target area.

As noted above, the retractor/stabilizer repositions and stabilizes a portion of a patient's panniculus. This facilitates access to the patient's internal anatomy on one side of the patient. For example, the retractor/stabilizers are beneficial for anterior hip replacements, venous access, femoral and inguinal hernia repair, saphenous vein harvesting, femoral artery access procedures, femoral nerve block, femoropopliteal bypass, urinary tract procedures, digestive disease procedures, infusion, injection, infiltration, and other procedures which do not require full access to the patient's abdomen (an issue which is solved by the retractor disclosed in our WO 2014/120746. Additionally, as noted above, the retractor/stabilizer increases access to the patient's airways (thoracic dilation and diaphragmatic excursion).

It has also been determined that when the retractor/stabilizer is utilized to retract, stabilize and reposition excessive and/or redundant tissue, additional tissue in the vicinity of the repositioned excessive and/or redundant tissue is also repositioned, and resulting in a reorientation of the surgical planes in the patient. Thus, for example, use of the retractor/stabilizer on a 340 lb. (~154 kg) patient may move the additional tissue to reorient the surgical planes of the patient such that the patient's surgical planes are more similar to the surgical planes of a 140 lb. (~63.5 kg) patient. This repositioning of this additional tissue reduces the distance between the patient's skin and targets beneath the skin. As noted above, this facilitates procedures such as imaging and radiation treatment. Current imaging (i.e., ultrasound, sonogram, etc.) techniques require that the excessive and/or redundant tissue above the imaging target be compressed and that a higher energy level be used than with patients having a normal body mass index. Currently, in radiation treatment, the power of the energy source must be increased to have sufficient energy at the target. The repositioning of this additional adipose tissue substantially eliminates the need for practitioners to compress the patient's flesh in the area to be imaged, and the need for higher energy is reduced for both imaging and radiation treatment. Similarly, the repositioning of the additional adipose tissue facilitates vascular access (such as in the groin area), because it should be easier for the practitioner to locate an artery (such as the femoral artery) or vein, and the practitioner may not need to push the needle through as much excessive and/or redundant tissue. For the same reasons, the repositioning of excessive and/or redundant tissue due to the retraction and stabilization of excessive and/or redundant tissue also aids in application of nerve blocks. Again, for the same reasons, even abdominal access is made easier because the amount of additional excessive and/or redundant tissue that the practitioner must cut through is reduced. For example, in the case of an anterior total hip arthroplasty, the distance from the dermis to the hip joint is reduced.

As can be appreciated from the above, the retractor/stabilizers can be quickly adhered to a patient. Affixing the retractor/stabilizer (actually affixing the top layer of the retractor/stabilizer) to a site with little or no adipose (such as the center of the back, the sternum, the groin, the bottom of a foot, etc.) creates an anchor point on the patient that is remote and across the patient's midline from the excessive and/or redundant tissue which the retractor/stabilizer retracts. The retractor/stabilizer is more efficient and more secure than retractor/stabilizers currently available. Further, when the retractor/stabilizer has been adhered to a patient, the retractor/stabilizer orients the patient's anatomy to a natural position and reorients the surgical plane.

From the forgoing, it can be seen that the retractor/stabilizer can be used for numerous types of procedures, including, but not limited to trauma care, imaging, mapping, electrode placement, monitoring, radiation therapy, cardiac catheterization, fetal ultrasound or sonography, laparotomies (hernias), incision and wound care, vascular access, nerve block and similar techniques used during interventional cardiology and radiology.

As can be appreciated, the retractor/stabilizer provides for a retractor/stabilizer which can be quickly and easily deployed and applied to retract and then stabilize excessive and/or redundant tissue of a patient. The use of the back cuts and face cuts which define the various tabs enable practitioners to easily remove the backing layer from the top layer without having to come into contact with the adhesive of the top layer. Additionally, the protected grasping areas allow the practitioners to manipulate the top layer, even after the backing layer has been removed to expose the adhesive, without contacting the adhesive. This substantially reduces the possibility of the practitioners' gloves from becoming stuck to the adhesive layer of the top layer. Further, as discussed, the retractor/stabilizer can be used during a medical procedure (i.e., surgery or examination) or can be used to facilitate healing of an incision, wound or infection on the patient that would otherwise be covered by excessive and/or redundant tissue.

In a broad sense, what is provided is an adhesive device, which in the preferred embodiment is formed from a single sheet of two-ply material which has an adhesive coated top layer and a backing layer. Inasmuch as the device is formed from a single sheet of two-ply material, the various portions or sections of the retractor/stabilizer body all have an upper layer and a backing layer. Thus, for example, the in body sections and their respective tabs, the backing layer remains associated with the backing layer of the body portion, and a cut is formed in the top layer to separate the top layer of the tab from its respective panel. Conversely, in the holding areas, the face or top cuts cause the backing layer of the holding areas to remain with the top layer as the backing layer is removed from the body. It is noted that the bottom cuts separating the bottom, inguinal, grab areas from the body also enables the backing layer of the inguinal grab panels to remain with the top layer when the backing layer removed from the body top layer in the positioning portion of the body.

Although the device has been described for use as a retractor/stabilizer, the tab design can have applications in other devices. For example, the tab design could be used in wound dressing bandages, labels, or other multi-layer applications.

It will be appreciated that the retractor/stabilizers disclosed herein are similar in function to the retractor of above noted WO 2014/120746. However, the retractor in WO 2014/120746 can be applied to substantially the entire width of the panniculus. The retractor/stabilizers disclosed herein, however, are applied to a right or left portion of the panniculus to retract one side or the other of the panniculus. In addition, the retractor/stabilizers are applied lower on the patient's torso. As described, the inguinal panel 20, 120 of the retractors 10, 110, for example, are adhered at the patient's inguinal crease and toward the patient's side. The retractor of WO 2014/120746, on the other hand, is applied in a more central (width-wise) location and is adhered at its bottom end to the radius of the panniculus, As various changes could be made in the above constructions without departing from the scope of the invention, it is intended that all matter contained in the above description or shown in the accompanying drawings shall be interpreted as illustrative and not in a limiting sense. For example, the tabs 30, 32, 34, 36, 130, 132 and 134 are all shown as out-board tabs (which extend from the body). However, the tabs could alternatively be inboard tabs (in which the outer edge of the tab is flush with the edge of the body. This variation is illustrative only.

The invention claimed is:

1. A retractor/stabilizer for repositioning and stabilizing excessive and/or redundant tissue; the retractor/stabilizer comprising a top layer and a backing layer; the top layer having an adhesive applied thereto which is exposed when the backing layer is separated from the top layer to enable the top layer to be applied to a surface; the retractor/stabilizer comprising:
    a body having a top edge, side edges and a bottom edge; said body comprising a positioning section and a main section; said main section comprising a main body portion and first and second anchor lobes extending from a main body portion; whereby said body is generally Y-shaped and outer edges of said first and second lobes are spaced outwardly from side edges of said positioning section and main body portion;
    a lower grasping panel proximate a lower edge of said body and proximate an outer end of said lower edge;
    at least one upper protected grasping/holding area located at an end of at least one of said anchor lobes such that said grasping/holding area is laterally offset from an edge of said lower grasping panel, said lower grasping panel being proximate a side of said body opposite said upper grasping/holding area such that when said retractor/stabilizer is stretched by pulling on said at least one protected grasping/holding area, said retractor will be stretched in a direction offset from a vertical axis of said retractor/stabilizer;
    said at least one upper protected grasping/holding area and said lower grasping panel each being defined in part by a back cut separating the backing layer of the lower grasping panel and the backing layer of the at least one grasping area from the backing layer of the body, the backing layer of the body defining at least one removable panel; whereby the backing layer of the lower grasping panel and the backing layer of the at least one grasping area remains with the at least one protected grasping/holding area and said lower grasping panel when the backing layer is removed from the body of the retractor/stabilizer.

2. The retractor/stabilizer of claim 1 including at least one tab portion associated with said at least one removable panel; the backing layer of the tab portion being integral with the backing layer of the body portion and the retractor/stabilizer including a cut in the top layer which separates the top layer of the tab portion from the top layer of the body portion.

3. The retractor/stabilizer of claim 2 wherein said lower grasping panel either extends from an outer end of said lower edge or comprises a bottom portion of said body.

4. The retractor/stabilizer of claim 1 including at least one anchor point at an upper end of said retractor/stabilizer on a side of said retractor/stabilizer opposite said at least one lower grasping panel.

5. The retractor/stabilizer of claim 4 including a grasping area proximate said at least one anchor point.

6. The retractor/stabilizer of claim 1 further including a lower grasping tab portion associated with said lower grasping panel; the backing layer of the lower grasping panel portion being integral with the backing layer of lower grasping panel and the retractor/stabilizer including a cut in the top layer which separates the top layer of the lower grasping tab portion from the top layer of the lower grasping panel.

7. The retractor/stabilizer of claim 1 further comprising at least one lower protected grasping/holding area located at an edge or corner of said retractor/stabilizer; said at least one lower grasping area being configured to be graspable by a technician without the technician contacting exposed adhesive of the top layer.

8. The retractor/stabilizer of claim 1 wherein said grasping area is integral with said body and is defined in part by a cut in the backing layer which divides the backing layer of the grasping area from the rest of the backing layer.

9. The retractor/stabilizer of claim 1 where the at least one upper protected grasping area is defined (1) by a portion of said top layer being folded or hemmed such that the top layer adhesive is turned back on itself, face to face, to produce the adhesive-free grasping area or (2) by a separate piece which is adhered to the retractor/stabilizer body.

10. A retractor/stabilizer for repositioning and stabilizing excessive and/or redundant tissue; the retractor/stabilizer comprising a top layer and a backing layer; the top layer having an adhesive applied thereto which is exposed when the backing layer is separated from the top layer to enable the top layer to be applied to a surface; the retractor/stabilizer comprising:

a body having a top edge, a first side edge, a second side edge, and a bottom edge; and at least one lower grasping panel proximate a lower edge of said body at an outer end of said bottom edge; said at least one lower grasping panel being defined in part by a back cut separating the backing layer of the lower grasping panel from the backing layer of the body; whereby the backing layer of the lower grasping panel remains with the lower grasping panel when the backing layer is removed from the body of the retractor/stabilizer; said lower grasping panel defining a lower anchor point;

a tab associated with said lower grasping panel; the backing layer of the tab portion being integral with the backing layer of lower grasping panel and the retractor/stabilizer including a cut in the top layer which separates the top layer of the tab portion from the top layer of the lower grasping panel such that the tab associated with the lower grasping panel is operable to remove the backing layer from the lower grasping panel; and an upper anchor point at said top edge of said body laterally and outwardly offset from one of side edges of said body.

11. The retractor/stabilizer of claim 10 wherein said retractor/stabilizer further comprises a back cut in the backing layer extending from one side to the other, to separate the backing layer into an upper panel and a lower panel; said at least one tab comprising at least one upper panel tab associated with the backing layer upper panel and at least one lower panel tab associated with the backing layer lower panel.

12. The retractor/stabilizer of claim 11 wherein the back cut defines a curvature that is adapted to simulate the curvature of a patient's abdomen or other anatomy of the patient.

13. The retractor/stabilizer of claim 11 wherein said retractor/stabilizer further comprises:

a lower panel back cut in the backing layer lower panel extending from the bottom edge to a point proximate the side-to-side back cut; said first lower panel back cut dividing the lower panel in to at least a lower panel positioning portion and a lower panel second portion;

a positioning portion tab associated with the lower panel positioning portion, said body including a cut in the top layer such that pulling on the positioning portion tab in a direction away from the top layer will remove the backing layer lower panel positioning portion from the top layer; and a lower panel second portion tab associated with the lower panel second portion; said body including a cut in the top layer such that pulling on the lower panel second portion tab in a direction away from the top layer will remove the backing layer lower panel second portion from the top layer.

14. The retractor/stabilizer of claim 11 wherein said at least one upper panel tab is located at one or both of said side edge and upper edge of said body.

15. The retractor/stabilizer of claim 10 further including an indicator/sensor adapted to monitor a parameter chosen from the group consisting of elongation and/or stretch of the retractor/stabilizer, ambient and physiological aspects of the patient's wound; said indicator/sensor being adapted to indicate of said monitored parameter exceeds or falls below a predetermined threshold.

16. The retractor/stabilizer of claim 15 wherein said ambient and physiological aspects include the presence of biological (i.e., bacterial or viral) agents, physiological data (i.e., blood pressure, skin temperature at the incision site, heart rate), or concentrations of specific chemicals, vapors or gases (such as $H_2O$, $O_2$ or $CO_2$).

17. The retractor/stabilizer of claim 15 wherein said indicator/sensor monitors elongation/stretch of the retractor/stabilizer, said indicator/sensor being a mechanical indicator incorporated into the retractor/stabilizer.

18. The retractor/stabilizer of claim 15 wherein said indicator/sensor is an electrical sensor; said sensor transmitting to a receiver a signal indicative of the parameter being monitored.

19. The retractor/stabilizer of claim 18 wherein said receiver issues a visual, tactile (vibratory) or audible alert if the monitored parameter exceeds or falls below said predetermined threshold.

20. The retractor/stabilizer of claim 19 wherein said receiver includes a transmitter to transmit data of the monitored parameter to a healthcare provider.

21. A retractor/stabilizer for repositioning and stabilizing excessive and/or redundant tissue; the retractor/stabilizer comprising a top layer and a backing layer; the top layer having an adhesive applied thereto which is exposed when the backing layer is separated from the top layer to enable the top layer to be applied to a surface; the retractor/stabilizer comprising:

a body having a top edge, side edges and a bottom edge; said body defining a bottom grasping area portion, a positioning portion above said grasping area portion, and a main portion above said positioning portion; the backing layer of said three portions being separated by back cuts; said main portion defining two spaced apart anchor points;

a tab portion associated each said portion of said body; the backing layer of the tab portion being integral with the backing layer of body portion and the retractor/stabilizer including a cut in the top layer which separates the top layer of the tab portion from the top layer of the body portion, such that pulling the tab will separate the backing layer from the top layer; and a protected upper grasping/holding area located at an upper end of said main portion along a first edge of said main portion; said upper grasping/holding area having an outer edge that is laterally and outwardly offset from said first edge of said main portion; said protected upper grasping/holding area being defined in part by a back cut separating the backing layer of the lower grasping panel and the backing layer of the upper grasping area from the backing layer of the body; whereby the backing layer of the upper grasping area remains with the upper protected grasping/holding area when the backing layer is removed from the body of the retractor/stabilizer.

22. The retractor/stabilizer of claim 21 wherein said body main portion includes a first part extending upwardly from said positioning portion and a second part extending to the left or right of said first part, such that an end of said second part is spaced horizontally from an edge of said first part.

23. The retractor/stabilizer of claim 21 wherein said body is generally Y-shaped and defines a first anchor lobe and a second anchor lobe.

24. The retractor/stabilizer of claim 23 wherein said at least one grasping area comprises a grasping area at an end of each of said lobes.

25. The retractor/stabilizer of claim 23 wherein one of said side edges of said body is generally straight.

26. The retractor/stabilizer of claim 23 wherein said retractor is generally symmetrical about an axis of said retractor body.

27. The retractor/stabilizer of claim 23 wherein said bottom portion of said body defines two spaced apart grasping areas.

28. The retractor/stabilizer of claim 21 wherein the top layer has a machine direction that runs generally diagonally to a vertical axis of the retractor/stabilizer, and wherein said protected upper grasping/holding area is positioned, such that when said retractor/stabilizer is applied to a patient, when said protected upper grasping/holding area is pulled, said retractor/stabilizer will stretch in a direction generally diagonal relative to the vertical axis and either generally parallel to or generally orthogonal to said machine direction.

* * * * *